(12) United States Patent
Allam et al.

(10) Patent No.: US 8,153,392 B2
(45) Date of Patent: Apr. 10, 2012

(54) METHOD(S) OF PREVENTING, ARRESTING, REVERSING AND TREATMENT OF ATHEROSCLEROSIS

(75) Inventors: Appa Rao Allam, Vsakhapatnam (IN); Undurti Narasimha Das, Shaker Heights, OH (US)

(73) Assignee: Undurti N Das, Shaker Heights, OH (US)

( * ) Notice: Subject to any disclaimer, the term of this patent is extended or adjusted under 35 U.S.C. 154(b) by 251 days.

(21) Appl. No.: 12/079,544

(22) Filed: Mar. 28, 2008

(65) Prior Publication Data
US 2008/0279925 A1 Nov. 13, 2008

Related U.S. Application Data

(60) Provisional application No. 60/928,319, filed on May 10, 2007.

(51) Int. Cl.
*C12Q 1/26* (2006.01)
*C12N 9/02* (2006.01)

(52) U.S. Cl. ........ 435/25; 435/189; 435/190; 435/252.3

(58) Field of Classification Search .................. 435/190, 435/252.3, 320.1; 514/44
See application file for complete search history.

(56) References Cited

U.S. PATENT DOCUMENTS 6,987,001 B2 * 1/2006 Hayden et al. .................. 435/25
2003/0077747 A1 * 4/2003 Hillman et al. .............. 435/69.1

* cited by examiner

*Primary Examiner* — Tekchand Saidha

(57) ABSTRACT

A method of detecting, diagnosing and prognosticating atherosclerosis by measuring the activities of $\Delta^6$ and $\Delta^5$ desaturases is described. It is suggested that enhancing the activities of $\Delta^6$ and $\Delta^5$ desaturases results in an increase in the plasma, leukocyte, platelet and endothelial cell levels of γ-linolenic, dihomo-γ-linolenic, arachidonic, stearidonic, 20:4 ω-3, eicosapentaneoic and docosahexaenoic acids and $PGE_1$ (prostaglandin $E_1$), prostacyclin ($PGI_2$), prostaglandin $I_3$ ($PGI_3$), lipoxins, resolvins, protectins, nitric oxide, and nitrolipids that prevent, arrest and reverse atherosclerosis. The invention is also directed to the delivery of proteins, peptides, lipids, lipoproteins, glycolipids, statins and troglitazones and their derivatives, and other compounds (synthetic or natural), cDNA clones and genes of $\Delta^6$ and $\Delta^5$ desaturases to enhance the activities of $\Delta^6$ and $\Delta^5$ desaturases in vivo to prevent, arrest, reverse and treat atherosclerosis.

4 Claims, 6 Drawing Sheets

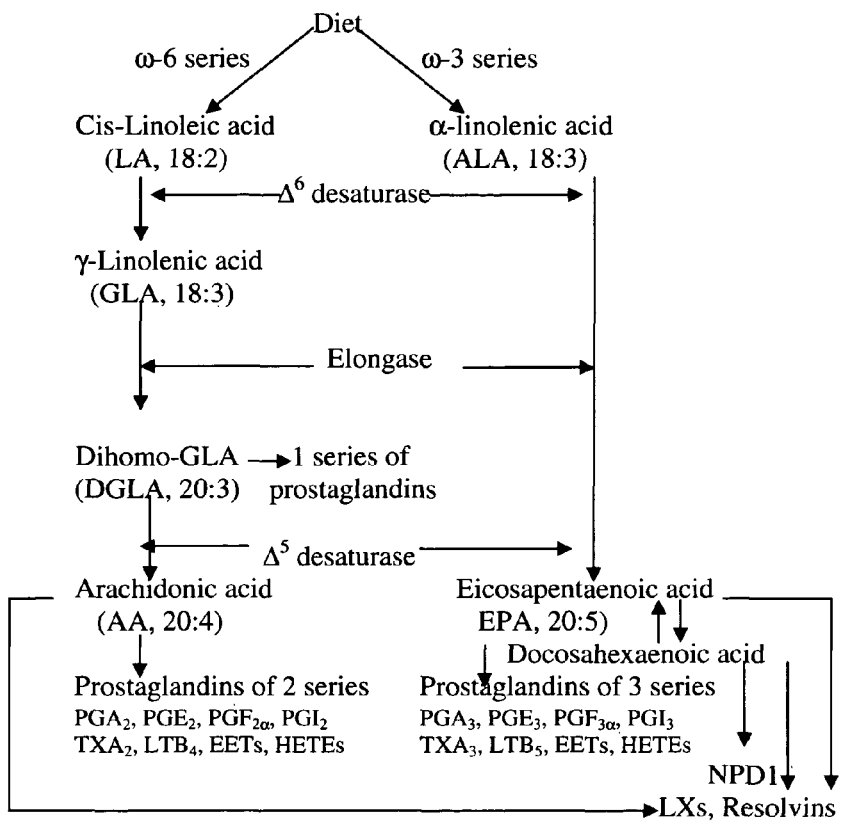
Figure 1. Metabolism of Essential Fatty Acids.

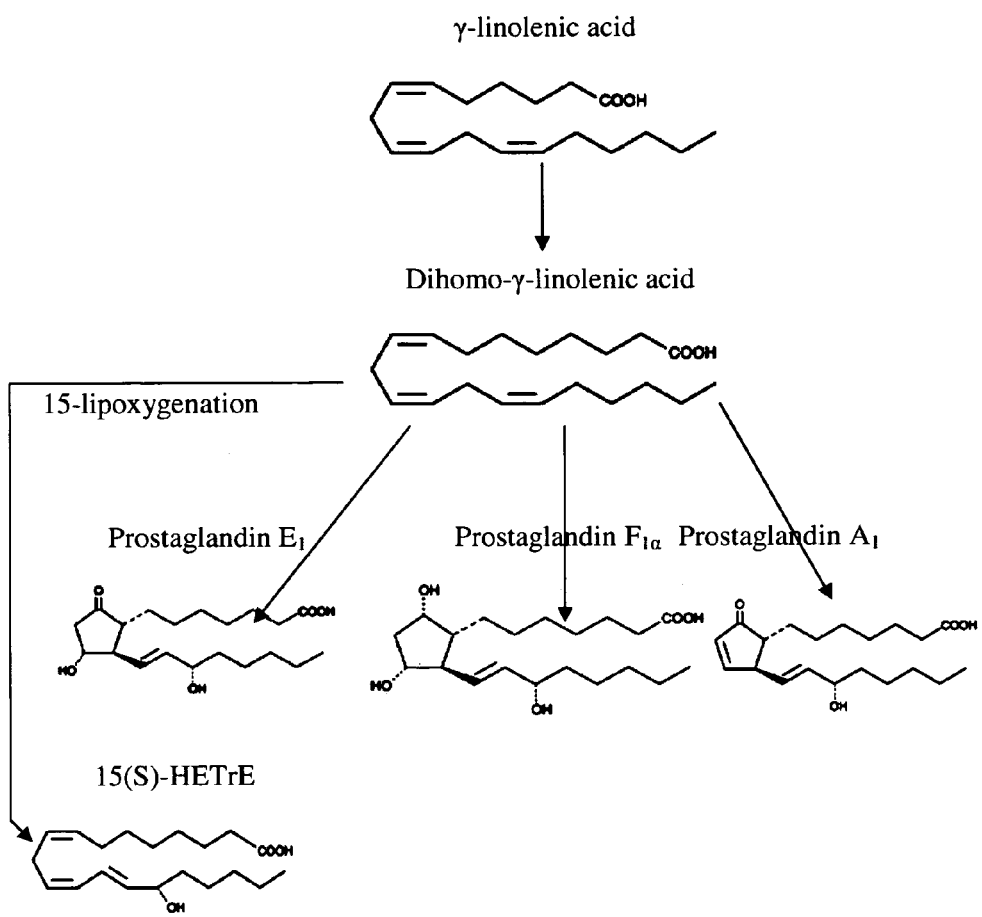
Figure 2. Scheme showing the formation of various prostaglandins from gamma-linolenic acid and dihomo-gamma-linolenic acid.

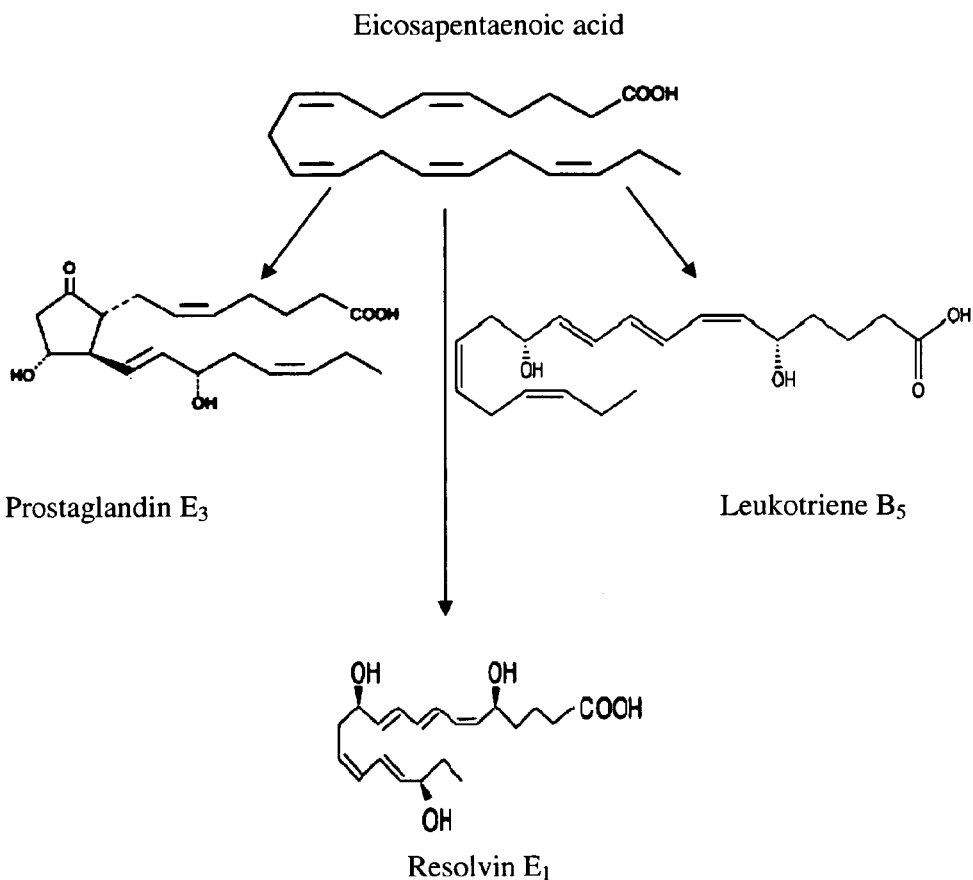

Figure 3a. Scheme showing various products formed from eicosapentaenoic acid.

Prostaglandin $E_3$ is a vasodilator, platelet aggregator, and has pro-inflammatory actions but is much less potent compared to $PGE_2$.

Leukotriene $B_5$ is a pro-inflammatory molecule but is much less potent compared to $LTB_4$.

Resolvin $E_1$ is a potent anti-inflammatory molecule and suppresses the formation of IL-6 and TNF-α.

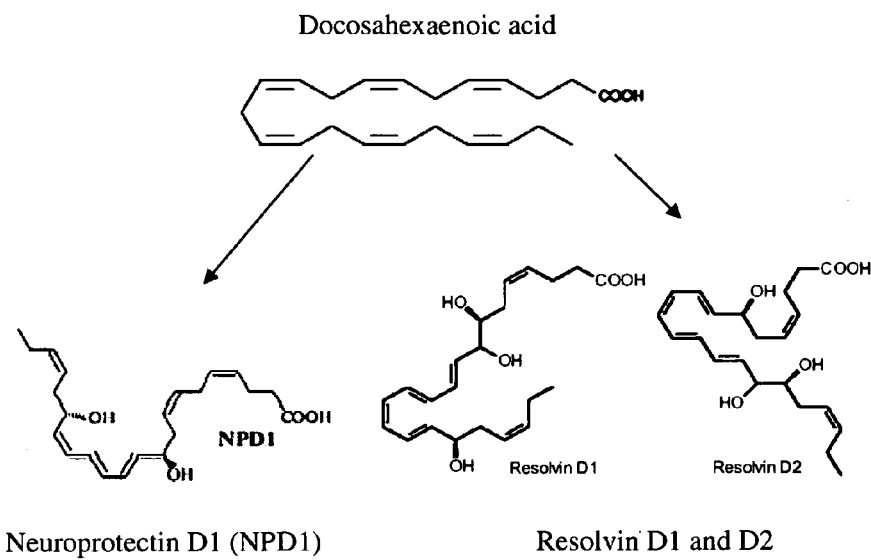
Figure 3b. Scheme showing various products formed from docosahexaenoic acid. NPD1 is an anti-inflammatory molecule and protects neuronal cells from TNF-α-induced apoptosis. Resolvins D1 and D2 are also anti-inflammatory compounds and are involved in healing of wounds and resolution of inflammation.

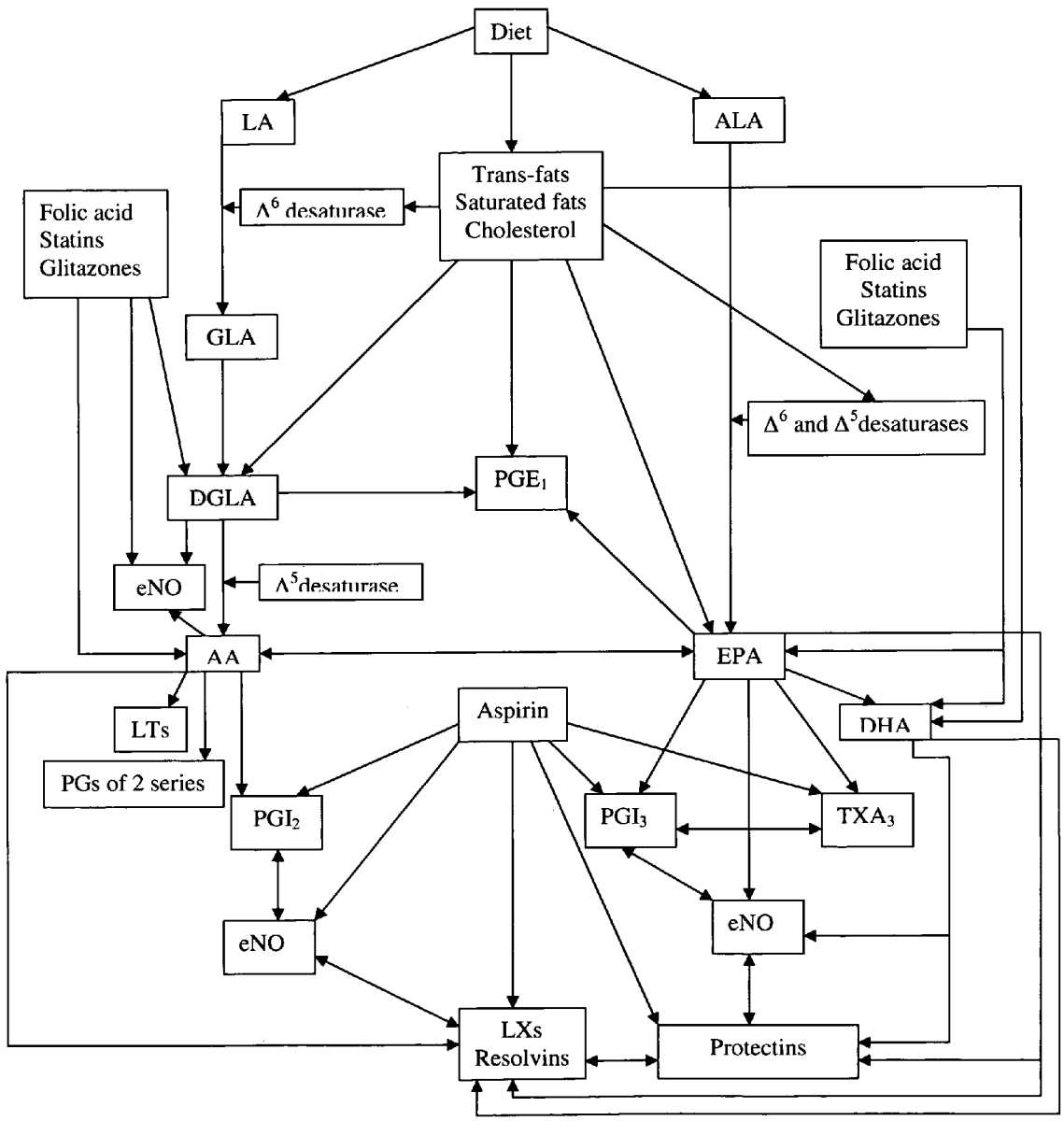
Figure 4. Scheme showing possible interaction(s) among ω-6, ω-3, and trans-fats, $PGE_1$, $PGI_2$, $PGI_3$, LXs, resolvins, and neuroprotectins and their relationship to atherosclerosis.

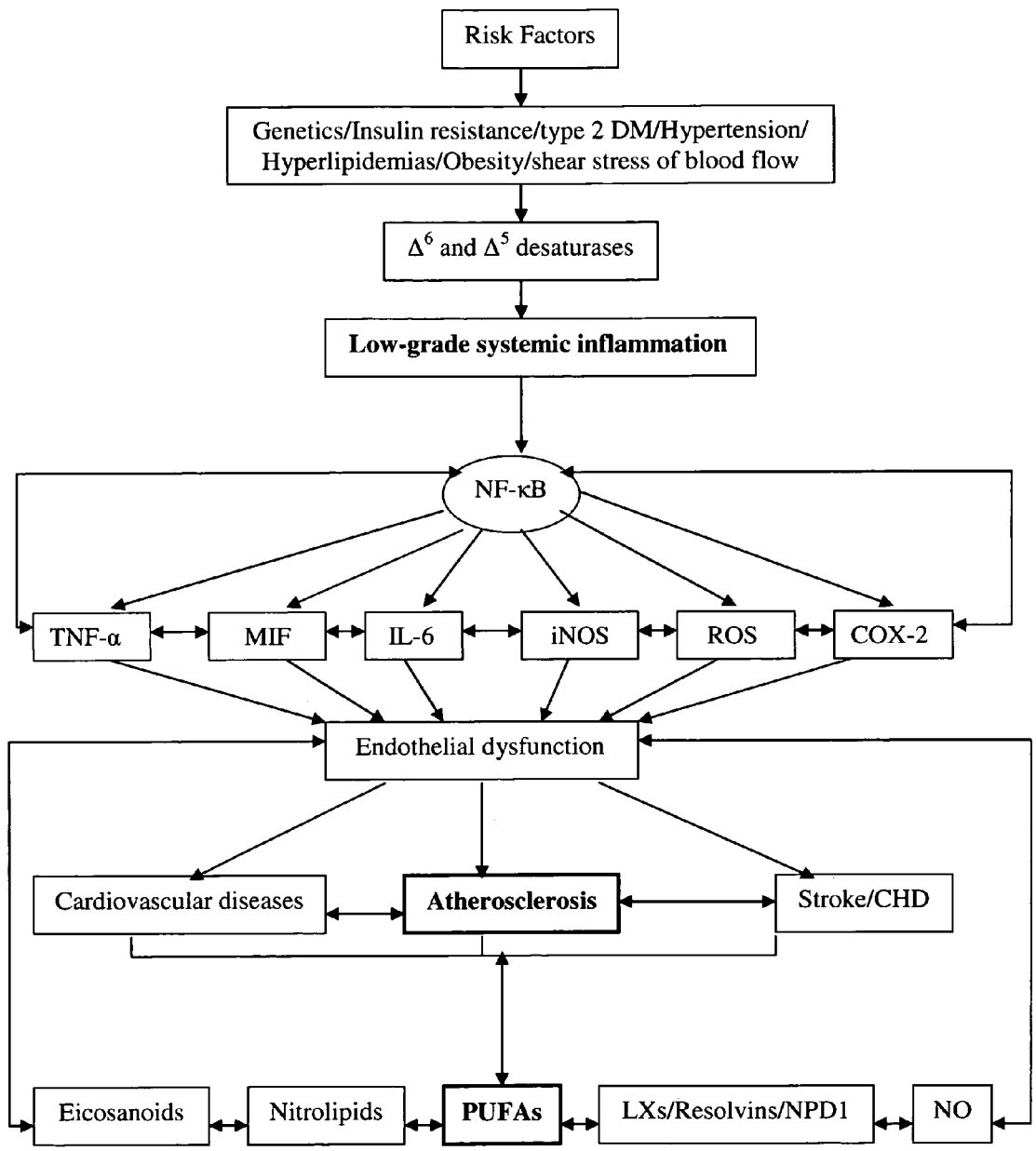
Figure 5. Scheme showing the relationship between various mediators of endothelial dysfunction and CHD/stroke and the role of PUFAs and their metabolites in these processes.

METHOD(S) OF PREVENTING, ARRESTING, REVERSING AND TREATMENT OF ATHEROSCLEROSIS

RELATED APPLICATIONS

This application claims the benefit of provisional patent application no. 60/928,319 filed on May 10, 2007.

BACKGROUND OF THE INVENTION

1. Field of Invention

The invention generally relates to a strategy or method of preventing, arresting, reversing and treatment of atherosclerosis. The invention, in particular, suggests that enhancing the activities of $\Delta^6$ and $\Delta^5$ desaturases such that the cell, tissue, and plasma levels of various polyunsaturated fatty acids (PUFAs) and, in particular that of endothelial cells lining the blood vessels will increase and this leads to arrest or prevention of atherosclerosis. The enhanced activities of $\Delta^6$ and $\Delta^5$ desaturases and various PUFAs will lead to increased production of their products such as prostacyclin ($PGI_2$), $PGI_3$, lipoxins, resolvins, protectins, $PGE_1$ (prostaglandin $E_1$) such that atherosclerotic process will be prevented, arrested, reversed and this will lead to efficient treatment of even established atherosclerosis and its associated conditions such as obesity, type 2 diabetes mellitus, coronary heart disease (CHD), hypertension, and metabolic syndrome X, and depression, and Alzheimer's disease. More particularly, the invention is directed to the efficacious use of proteins, peptides, lipids, lipoproteins, glycolipids, synthetic chemicals such as statins and their derivatives, troglitazones and their derivatives, cDNA clones of $\Delta^6$ and $\Delta^5$ desaturases, genes of $\Delta^6$ and $\Delta^5$ desaturases, for the prevention, arrest, reversal and treatment of atherosclerosis. It is suggested that decreased or defective either qualitative or quantitative activity of $\Delta^6$ and $\Delta^5$ desaturases is responsible for atherosclerosis. Furthermore, the invention also teaches that appropriate and desired amount of activation of $\Delta^6$ and $\Delta^5$ desaturases would occur leading to the synthesis, formation and accumulation of various polyunsaturated fatty acids and the synthesis, formation and release of their products such as prostacyclin ($PGI_2$), $PGI_3$, lipoxins, resolvins, protectins, $PGE_1$ (prostaglandin $E_1$), and nitric oxide (NO) would occur leading to the prevention, arrest, reversal and treatment of atherosclerosis. This invention also teaches efficient use of methods to enhance the activity of $\Delta^6$ and $\Delta^5$ desaturases specifically in the cerebral blood vessels by various synthetic and natural compounds which are able to cross blood brain barrier (BBB) when administered orally, parentarally or by any other route and enter brain in sufficient quantities to produce their desired actions.

2. Description of the Related Art

Atherosclerosis, the major underlying cause for coronary heart disease (CHD), is a dynamic process. In majority of the instances, hyperlipidemia, diabetes mellitus, hypertension, and obesity are the main risk factors for the development of atherosclerosis and CHD. Several studies revealed that in CHD, hypertension, diabetes mellitus, hyperlipidemias, and obesity, EFA (essential fatty acids) metabolism is abnormal such that plasma and tissue concentrations of γ-linolenic acid (GLA), dihomo-GLA (DGLA), arachidonic acid (AA), eicosapentaenoic acid (EPA), and docosahexaenoic acid (DHA) in the phospholipid fraction are low (1-8). Increased intake of polyunsaturated fatty acids (PUFAs especially in the form of GLA, DGLA, EPA and DHA) protects against the development of these diseases both in experimental animals (9-12) and humans (13), though the exact mechanism of this protective action is unclear. GLA, DGLA, AA, EPA, and DHA form precursors to prostaglandin $E_1$ ($PGE_1$), prostacyclin ($PGI_2$), $PGI_3$, lipoxins (LXs), resolvins, neuroprotectin D1 (NPD1), enhance NO generation, and interact with NO to form nitrolipids that have anti-inflammatory actions, prevent platelet aggregation, inhibit leukocyte activation and augment wound healing and resolve inflammation that may account for their beneficial actions. This implies that an altered EFA metabolism in the form of a block in the activity of $\Delta^6$ and $\Delta^5$ desaturases, which are essential for the formation of long-chain metabolites from dietary linoleic acid (LA, 18:2 ω-6) and α-linolenic acid (ALA, 18:3 ω-3), could lead to reduced formation of $PGE_1$, $PGI_2$, NO, LXs, resolvins, and nitrolipids that could initiate and aggravate atherosclerosis.

Atherosclerosis is a Low-Grade Systemic Inflammatory Condition

Atherosclerosis is common both in the developed and developing countries. An increase in the plasma concentrations of C-reactive protein (CRP), tumor necrosis factor-α (TNF-α), interleukin-6 (IL-6), myeloperoxidase (MPO), lipoprotein associated phospholipase $A_2$ ($Lp-PLA_2$), and lipid peroxides occurs in atherosclerosis suggesting that it is a low-grade systemic inflammatory condition (14-17). Myeloperoxidase (MPO), an abundant leukocyte enzyme; CRP, produced by endothelial cells and liver; lipoprotein-associated phospholipase $A_2$ ($Lp-PLA_2$), produced by macrophages, is expressed in greater concentrations in atherosclerotic lesions (16). Elevated $Lp-PLA_2$ is significantly and independently associated with a 2-fold higher risk for CHD events including myocardial infarction, neovascularization, and death from cardiac disease (16, 17).

Low circulating NO (nitric oxide) levels-due to its decreased production by endothelial cells, increased generation of reactive oxygen species (ROS) by infiltrating leukocytes and macrophages (18-22), and decreased anti-oxidant content of the endothelia cells at atherosclerosis-prone areas of the blood vessels due to their exposure to increased ROS leads to an imbalance between the pro- and anti-oxidant status that is tilted more in favor of pro-oxidants leads to endothelial damage (18).

Mediators of Inflammation in Atherosclerosis

There are many chemical mediators of inflammation. Some of the important mediators of inflammation include: histamine, serotonin, lysosomal enzymes, prostaglandins (PGs), leukotrienes (LTs), thromboxanes (TXs), platelet activating factors (PAFs), ROS, NO, HOCL, various cytokines, kinin system, coagulation/fibrinolysis system, and complement system. NO has both pro- and anti-inflammatory actions depending on the source and the local concentration. Histamine, serotonin, bradykinin, complement system and coagulation cascade are well known for their involvement in infections, inflammatory process and sepsis and septic shock. The major cellular sources of these mediators are platelets, neutrophils, monocytes/macrophages, mast cells, mesenchymal cells such as endothelium, smooth muscle, fibroblasts, and most epithelia. It is interesting to note that one mediator triggers the release of another mediator that acts on the target tissue. These secondary mediators either potentiate the action of the initial mediator or paradoxically abrogate its action. Thus, the ultimate degree of inflammation depends on the balance between such pro- and anti-inflammatory mediators. In some instances, anti-inflammatory chemicals or signals initiated may not only act on the target tissue but also on other tissues to suppress inflammation. Once released or activated, most of these mediators are inactivated or decay quickly. For instance, AA and its metabolites have a short half-life, whereas specific or non-specific enzymes inactivate kinins. On the other hand, ROS and NO are scavenged by specific or non-specific antioxidants (23).

Under normal physiological conditions, a balance is maintained between pro- and anti-inflammatory molecules. This delicate balance is tilted more towards the pro-inflammatory molecules in atherosclerosis leading to its initiation and progression. If this altered balance between pro- and anti-inflammatory molecules is restored to normal, then it is likely that atheroslcerosis process could be prevented. One such important source of anti-inflammatory molecules is EFAs. Recent studies showed that GLA, DGLA, AA, EPA, and DHA, which are polyunsaturated fatty acids (PUFAs), are of benefit in atherosclerosis. The role of EFAs and their products in inflammation is complex.

Metabolism of Essential Fatty Acids

Essential fatty acids (EFAs) are important constituents of all cell membranes and alter membrane fluidity and thus, determine and influence the behaviour of membrane-bound enzymes and receptors. EFAs are essential for humans and as are not synthesized in the body; have to be obtained in our diet (1). The two EFAs are $\omega$-6 cis-linoleic acid (LA, 18:2) and the $\omega$-3 $\alpha$-linolenic acid (ALA, 18:3). LA is converted to $\gamma$-linolenic acid (GLA, 18:3, n-6) by the enzyme $\Delta^6$ desaturase and GLA is elongated to form dihomo-GLA (DGLA, 20:3, $\omega$-6), the precursor of the 1 series of prostaglandins (PGs). DGLA can also be converted to arachidonic acid (AA, 20:4, $\omega$-6) by the enzyme $\Delta^5$ desaturase. AA forms the precursor of 2 series of PGs, TXs and the 4 series of LTs. ALA is converted to EPA (20:5, $\omega$-3) by $\Delta^6$ and $\Delta^5$ desaturases. EPA forms the precursor of the 3 series of PGs, TXs and the 5 series of LTs. LA, GLA, DGLA, AA, ALA, EPA and DHA (22:6, $\omega$-3) are all PUFAs, but only LA and ALA are EFAs (see FIGS. 1-3 for metabolism of EFAs). AA and EPA also are converted to their respective LTs. PGs, TXs, and LTs, which play an important role in atherosclerosis, CHD, bronchial asthma, inflammatory bowel disease, and other inflammatory conditions (1).

Eicosanoids (all types of PGs, LTs and TXs formed from PUFAs are termed as eicosanoids) bind to G protein-coupled receptors on many cell types and mediate virtually every step of inflammation, are found in inflammatory exudates, and their synthesis is increased at sites of inflammation. Non-steroidal anti-inflammatory drugs (NSAIDs) such as aspirin inhibit cyclo-oxygenase (COX) activity that may be responsible for their anti-inflammatory action.

(a) Cyclo-Oxygenase (COX) and Lipoxygenase (LO) Pathways

There are two cyclo-oxygenase enzymes, the constitutively expressed COX-1 and the inducible enzyme COX-2 that leads to the generation of prostaglandins (PGs). Based on the role of eicosanoids in inflammation, COX-2 inhibitors have been developed that are expected to reduce inflammation in vivo without gastric side effects. But, recent studies showed that COX-2 inhibitors are likely to increase the incidence of coronary heart disease (CHD)/cardiovascular disease (CVD). Different types of PGs are formed depending on the substrate fatty acid from which they are derived. Different types of PGs have different actions and some times diametrically opposite actions. For example, $PGE_2$, $PGF_{2\alpha}$, thromboxane $A_2$ ($TXA_2$), and leukotrienes (LTs) have pro-inflammatory actions whereas $PGE_1$ and prostacyclin ($PGI_2$) may show anti-inflammatory actions. Furthermore, the distributions of COX-1 and COX-2 enzymes have restricted tissue distribution. For instance, platelets contain thromboxane synthetase; and hence $TXA_2$, a potent platelet-aggregator and vasoconstrictor, is the major product in these cells. In contrast, vascular endothelial cells lack thromboxane synthetase but possess $PGI_2$ synthetase that leads to $PGI_2$, a potent platelet anti-aggregator and vasodilator. The balance between $TXA_2$ and $PGI_2$ plays a significant role in atherosclerosis and thrombus formation in coronary and cerebral blood vessels.

COX-2 enzyme is absent in most tissues under normal "resting" conditions and is expressed in response to pro-inflammatory stimuli, whereas COX-1 is constitutively expressed in most tissues. This suggests that PGs produced by COX-1 serve a homeostatic function (such as fluid and electrolyte balance in the kidneys, cytoprotection in the gastrointestinal tract) and are also involved in inflammation, whereas COX-2 stimulates the production of the PGs that are involved in inflammatory reactions.

There are 3 types of lipoxygenases and are present in only a few types of cells. 5-lipoxygenase (5-LO) is the predominant enzyme in neutrophils. The main product, 5-HETE, which is chemotactic for neutrophils, is converted into leukotrienes (LTs). $LTB_4$ is a potent chemotactic agent and activator of neutrophils and induces aggregation and adhesion of leukocytes to vascular endothelium, generation of ROS, and release of lysosomal enzymes. The cysteinyl-containing leukotrienes $C_4$, $D_4$, and $E_4$ ($LTC_4$, $LTD_4$, and $LTE_4$) induce vasoconstriction, bronchospasm, and vascular permeability. LTs are more potent than histamine in increasing vascular permeability and causing bronchospasm. LTs mediate their actions by binding to cysteiny leukotreine 1 (CysLT1) and CysLT2 receptors.

Lipoxins (LXs) are generated from AA, EPA and DHA by transcellular biosynthetic mechanisms (involving two cell populations). Leukocytes, particularly neutrophils, produce intermediates in LX synthesis, and these are converted to LXs by platelets interacting with leukocytes. $LXA_4$ and $LXB_4$ are generated by the action of platelet 12-lipoxygenase on neutrophil-derived $LTA_4$. Cell-cell contact enhances transcellular metabolism, and blocking adhesion inhibits LX production. LXs inhibit leukocyte recruitment, the cellular components of inflammation, neutrophil chemotaxis and leukocyte adhesion to endothelium (1, 24). LXs serve as endogenous negative regulators of LT synthesis and action and thus play a role in the resolution of inflammation. The inverse relationship that exists between the amounts of LXs and LTs formed suggests that the balance between these two molecules is crucial in the determination of degree of inflammation and in its final resolution.

(b) Modulators of Metabolism of EFAs

Dietary LA and ALA are metabolized by the enzymes $\Delta^6$ and $\Delta^5$ desaturases to their respective metabolites as shown in FIG. 1. LA, ALA, and oleic acid (OA, a $\omega$-9 fatty acid) are metabolized by the same set of $\Delta^6$ and $\Delta^5$ desaturases and elongases. As a result, these 3 series compete with one another for the same set of enzymes, though the enzymes seem to prefer $\omega$-3 to $\omega$-6 and $\omega$-6 over $\omega$-9 ($\omega$-3>$\omega$-6>$\omega$-9). Hence, under normal physiological conditions the metabolites of $\omega$-9 are formed only in trivial amounts in the cells. Thus, presence of significant amounts of 20:3 $\omega$-9 indicates EFA (LA and ALA) deficiency. The activities of $\Delta^6$ and $\Delta^5$ desaturases are slow in humans ($\Delta^5$>$\Delta^6$). As a result, the conversion of LA and ALA to their respective metabolites may be inadequate under certain conditions. In such instance, it is necessary to supplement GLA and DGLA (to bypass $\Delta^6$ desaturase) and AA and EPA and DHA (to bypass $\Delta^6$ and $\Delta^5$ desaturases). Generally, supplementation of AA is not necessary since; it can be obtained from the diet. Western diet is rich in ω-6 fatty acids compared to ω-3 fatty acids (ω-6 to ω-3 ratio is 10:1), whereas the recommended ratio is ~1:1 (1).

Saturated fats, cholesterol, trans-fatty acids, alcohol, adrenaline, and glucocorticoids inhibit $\Delta^6$ and $\Delta^5$ desaturases (1, 25, 26). Pyridoxine, zinc, nicotinic acid, and magnesium are co-factors for normal $\Delta^6$ desaturase activity. Insulin activates $\Delta^6$ desaturase whereas diabetics have reduced $\Delta^6$ desaturase activity. The activity of $\Delta^6$ desaturase falls with age. Oncogenic viruses and radiation inhibit $\Delta^6$ desaturase activity. Total fasting, protein deficiency, and a glucose-rich diet reduce, whereas fat-free diet and partial caloric restriction enhance $\Delta^6$ desaturase activity. Activity of $\Delta^6$ and $\Delta^5$ desaturases are regulated by sterol regulatory element binding protein-1 (SREBP-1) and peroxisome proliferator-activated receptor-α (PPAR-α), two reciprocal transcription factors for fatty acid metabolism, and some of their (SREBP-1 and PPAR-α) lipogenic functions are brought about by their action on PUFAs (27).

Activities of $\Delta^6$ and $\Delta^5$ desaturases are decreased in diabetes mellitus, hypertension, hyperlipidemia, and metabolic syndrome X. Trans fats interfere with the metabolism of EFAs and promote inflammation, atherosclerosis and CHD (1, 28). The pro-inflammatory action of trans fats is due to their ability to interfere with EFA metabolism. Several PUFAs, especially EPA and DHA inhibit the production of pro-inflammatory cytokines: interleukin-6 (IL-6), tumor necrosis factor-α (TNF-α), IL-1, and IL-2 (1). Saturated fatty acids and cholesterol interfere with the metabolism of EFAs and thus, promote the production of pro-inflammatory cytokines, which explains their ability to cause atherosclerosis and CHD. Thus, trans fats, saturated fats, and cholesterol have pro-inflammatory actions whereas PUFAs possess anti-inflammatory properties. Interference with the metabolism of EFAs by saturated fats, cholesterol and trans fats reduces the formation of GLA, DGLA, AA, EPA, and DHA that are essential for the formation of beneficial prostacyclin ($PGI_2$), $PGI_3$, lipoxins, and resolvins. Deficiency and/or absence of $PGI_2$, $PGI_3$, lipoxins and resolvins initiate and accelerate atherosclerosis due to persisting inflammation.

(c) Formation of Lipoxins, Resolvins, and Neuroprotectin D1

PUFAs also give rise to lipoxins (LXs) and resolvins, which have potent anti-inflammatory actions (1). Aspirin converts AA, EPA and DHA to form aspirin-triggered 15 epimer LXs (ATLs) that inhibit acute inflammation (1, 29-31). Acetylation of COX-2 enzyme remains active in situ to generate 15R-hydroxy-eicosa-tetraenoic acid (15R-HETE) from AA that is converted by activated PMNs to the 15-epimeric lipoxins (LXs) (1, 29, 30). These 15-epimeric LXs prevent local inflammation on the vessel wall by regulating the motility of PMNs, eosinophils, and monocytes (1). COX-2 enzyme is essential for the formation of LXs, whose deficiency leads to an interaction between PMN and endothelial cells that results in endothelial damage, initiation and progression of atherosclerosis.

Compounds similar to 15R-HETE and 15-epimeric LXs are also formed from EPA and DHA. These include conversion of EPA to 18R-HEPE (18R-hydroxy-eicosapentaenoic acid), 18-HEPE, and 15R-HEPE. Activated human PMNs, in turn, convert 18R-HEPE to 5,12,18R-triHEPE and 15R-HEPE to 15-epi-$LXA_5$ by 5-lipoxygenase. Both 18R-HEPE and 5,12,18R-triHEPE inhibited $LTB_4$-stimulated PMN transendothelial migration similar to 15-epi$LXA_4$. 5,12,18R-triHEPE competed with $LTB_4$ for its receptors and inhibited PMN infiltration, and thus, 5,12,18R-triHEPE suppresses LT-mediated responses when present at the sites of inflammation (1, 29-32).

Murine brain cells transformed enzymatically DHA to 17R series of hydroxy DHAs (HDHAs) that, in turn, is converted enzymatically by PMNs to di- and tri-hydroxy containing docosanoids (1, 33). Similar small molecular weight compounds (similar to HDHAs) are generated from AA and EPA. Thus, 15R-hydroxy containing compounds are formed from AA, 18R series from EPA, and 17R-hydroxy series from DHA that have potent anti-inflammatory actions and induce resolution of the inflammatory process and hence are called "resolvins" (see FIG. 3). Resolvins inhibited cytokine generation, leukocyte recruitment, leukocyte diapedesis, and exudate formation. AA, EPA, and DHA-derived resolvins inhibited brain ischemia-reperfusion injury. 10,175-dihydroxydocosatriene derived from DHA termed as neuroprotectin D1 (NPD1) reduced infiltration of PMNs, showed anti-inflammatory and neuroprotective properties (34). NPD1 inhibited oxidative stress-induced apoptosis of human retinal pigment epithelial cells (35). Both LXs and NPD1 enhanced wound healing (36), and promoted brain cell survival (37, 38). Thus, lipoxins and resolvins formed from AA, EPA, and DHA have cardio-protective, neuroprotective, and other cyto-protective actions. In view of these evidences, it is possible that whenever the plasma and tissue levels of AA, EPA, and DHA are low the formation of LXs, resolvins and NPD1 are likely to be inadequate and this may impair myocardial-healing process after myocardial infarction/injury. Furthermore, since LXs, resolvins and NPD1 have anti-inflammatory actions inadequate formation of these important molecules could lead to inappropriate inflammatory process in diseases of low-grade systemic inflammatory diseases: obesity, metabolic syndrome X, hypertension, CHD/CVD. This is especially so, since LXs, resolvins and NPD1 suppress the production of pro-inflammatory cytokines. Hence, local deficiency of LXs, resolvins and NPD1 may have a significant role in atheroslcerosis, CHD/CVD, and metabolic syndrome X. In view of this, it will be interesting to study the relationship between plasma hs-CRP, Lp-$PLA_2$, various pro-inflammatory cytokines and LXs, resolvins and NPD1 in CHD/CVD. The fact that from the same precursor namely: AA, EPA, and DHA both pro- and anti-inflammatory molecules can be derived (see FIGS. 2-3) are not only surprising but also have significant clinical implications. Thus, understanding the molecular mechanisms by which the formation of pro- and anti-inflammatory molecules from AA, EPA, and DHA is controlled is essential to develop newer therapeutic strategies for atherosclerosis, CHD/CVD and other inflammatory conditions such as rheumatoid arthritis, lupus, scleroderma, and sepsis.

(d) Nitrolipids

NO can react with PUFAs to yield their respective nitroalkene derivatives that can be detected in plasma. These nitroalkene derivatives, termed as nitrolipids, produce vascular relaxation, inhibit neutrophil degranulation and superoxide formation, and inhibit platelet activation (39-41). Nitrolipids have endogenous PPAR-γ ligand activity and release NO (41). These actions of nitrolipids prevent platelet aggregation, thrombus formation and atherosclerosis, and prevent inflammation. This implies that nitrolipids have a significant role in low-grade systemic inflammatory conditions such as atherosclerosis and CHD/CVD. Since, nitrolipids are present both in the plasma and urine in substantial amounts, it could be measured in various clinical conditions. These evidences suggest that PUFAs not only form precursors to various eicosanoids, resolvins, LXs, and NPD1 but also react with NO to form nitrolipids that have platelet anti-aggregatory action, prevent thrombus formation and thus, arrest atherosclerosis. Nitrolipids also have anti-inflammatory actions.

Cross Talk Between Platelets, Leukocytes and Endothelial Cells

Based on the preceding discussion, it is clear that there is a close interaction between platelets, leukocytes and endothelial cells. This cross talk between these three types of cells could ultimately determine the initiation and progression of atherosclerosis and thrombosis. For instance, under normal conditions, endothelial cells produce adequate amounts of $PGE_1$ from DGLA; $PGI_2$ from AA; LXs and resolvins from AA, EPA and DHA; and NO from L-arginine such that the pro-inflammatory and pro-atherosclerotic events are successfully abrogated. Some of these pro-inflammatory and pro-atherogenic stimuli include: hemodynamic forces, hyperlipidemia, hypertension, smoking, etc. These factors induce the expression of pro-inflammatory genes that initiate and accelerate atherosclerosis at the points of shear stress, enhance infiltration of intima by leukocytes and macrophages, cause low-level activation of NF-κB and elevated expression of VCAM-1 and ICAM-1, IL-1, IL-6, MCP-1, as well as antioxidant genes glutathione peroxidase and glutathione-S-transferase 2, and pro-inflammatory eicosanoids such as $TXA_2$, $PGE_2$, $PGF_{2\alpha}$, LTs, and other PGs, TXs, and LTs, and increased production and release of free radicals and UCP (uncoupling proteins) expression occurs in endothelial cells, platelets, and leukocytes in atherosclerosis-susceptible regions, and endothelial cells themselves may show changes in cell shape and proliferation. These events can be prevented and atherosclerosis process is arrested by the production of adequate amounts of $PGE_1$, $PGI_2$, $PGI_3$, LXs, resolvins, NO, and anti-inflammatory cytokines such as IL-4, IL-10, TGF-β by endothelial cells, provided there are adequate stores of respective precursors of various PUFAs and L-arginine and their respective enzymes. This suggests that under physiological conditions a delicate balance is maintained between pro- and anti-inflammatory and pro and anti-atherosclerotic factors. When this delicate balance is tilted more towards pro-atherosclerotic and pro-inflammatory factors, atherosclerosis occurs.

Leukocytes in CHD and Atherosclerosis

Leukocytosis is a marker of inflammation. Recent studies revealed that higher leukocyte count could be associated with a greater cardiovascular risk (42). In this context, it is important to note that infiltration of intima by leukocytes and macrophages is one of the earliest events to occur in atherosclerosis. Elevated LDL, hypertension, hyperglycemia, and other systemic factors initiate and accelerate atherosclerosis. Despite the fact that the entire vascular endothelium is exposed to these systemic factors, it is common knowledge that atherosclerotic lesions occur in a patchy manner and develop preferentially at bifurcations, branch points, and inner curvatures of arteries, suggesting that local factors play a major role in the development of atherosclerosis. Hemodynamic forces to these regions may induce the expression of pro-inflammatory genes (43-45) that may initiate and accelerate atherosclerosis at these points of shear stress. Experiments performed in normocholesterolemic C57BL/6 mice and rabbits revealed that low-level activation of NF-κB and elevated expression of VCAM-1 and ICAM-1 occurs in endothelial cells in atherosclerosis-susceptible regions of the ascending aorta (46-48). Gene expression profiling studies revealed that at the sites of atheroslcerosis-prone regions endothelial cells showed upregulation of pro-inflammatory genes IL-1, IL-6, MCP-1, as well as antioxidant genes glutathione peroxidase and glutathione-S-transferase 2, and endothelial cells themselves demonstrated changes in cell shape and proliferation (46, 49). Endothelial cells in these atherosclerosis-prone regions of aorta showed increases in LDL and cholesterol transport and retention (50-52). Furthermore, intimal accumulation of LDL and its oxidation products preceded monocyte recruitment into early atherosclerotic lesions, suggesting that lipid accumulation triggers inflammatory response characterized by upregulation of the expression of chemokines and adhesion molecules in the lesion-prone areas in the intima that contributes to leukocyte accumulation and atherosclerotic lesion formation (53-56). These evidences imply that at atheroslcerosis-prone regions of the normal intima inflammatory response is triggered on introduction of atheroslcerotic risk factors (such as hyperlipidemia, hypertension, etc.) that leads to upregulation of several proinflammatory genes including various adhesion molecules and chemokines, which mediate accumulation of leukocytes and initiation and perpetuation of atherosclerosis. Jongstra-Bilen et al (56) showed that considerable lower numbers of intimal CD68+ leukocytes were found in inbred atheroslcerosis-resistant mice compared to wild type, and the predominant mechanism for the accumulation of these leukocytes was due to continued recruitment of bone marrow-derived blood monocytes, suggestive of low-grade inflammation. In contrast, intimal CD68+ leukocytes were reduced in VCAM-1-deficient mice suggesting that in the intima of atherosclerosis-predisposed regions increased expression of proinflammatory genes occurs. In summary these results indicate that healthy endothelial cells are able to prevent excess expression of adhesion molecules, resist increases in LDL and cholesterol transport and retention, abrogate activation of NF-κB and the induction of expression of pro-inflammatory genes induced by hemodynamic forces at bifurcations, branch points, and inner curvatures of arteries, regions that are prone for atherosclerosis due to enhanced infiltration by monocytes, CD68+ leukocytes, and macrophages. This implies that under normal physiological conditions healthy endothelial cells are able to produce factors/molecules that can successfully counter pro-atherosclerotic events. Essential fatty acids and their beneficial metabolites is one such factor that appears to be critical for maintaining endothelial structural integrity and function.

Uncoupling Protein-1, Essential Fatty Acids, and Atherosclerosis

The patchy manner in which atherosclerosis occurs suggests that arterial walls undergo regional disturbances of metabolism that include the uncoupling of respiration and oxidative phosphorylation, which may be characteristic of blood vessels being predisposed to the development of atheroslcerosis (57). Oxidative stress is implicated in atherosclerosis. Mitochondrial electron transport accounts for most reactive oxygen species (ROS) production (58). ROS production occurs during mitochondrial respiration that also produces energy in the form of ATP, resulting from ADP phosphorylation, as electrons at complex I and III react with molecular oxygen to form superoxide (59). Uncoupling proteins (inner mitochondrial membrane anion transporters) allow protons to leak back into the mitochondrial matrix, thereby decreasing the potential energy available for ADP phosphorylation and ROS generation. Superoxide anion activates uncoupling proteins (60, 61) that, in turn, limit further superoxide generation by dissipating protonmotive force and thus, decreases oxidative stress. This is supported by the observation that uncoupling decreases glucose-induced ROS formation and abrogates pathways associated with vascular damage in endothelial cells in vitro (62). In contrast, UCP-2 in macrophages decreases ROS and atheroslcerosis (63). Although, these results appear to be in conflict with the proposal that inefficient vascular metabolism is detrimental, it is known that uncoupling agents produce smooth muscle contraction and cause hypertension (64), and it was reported that respiratory uncoupling is increased in the aortae of experimental animals that are susceptible to atherosclerosis (57). These results imply that the efficiency of vascular wall energy metabolism could be a determinant of atherosclerotic lesion development. Bernal-Mizrachi et al (65) showed that UCP-1 expression in aortic smooth muscle cells causes hypertension and increases atheroslcerosis without affecting cholesterol levels. This increase in UCP-1 expression also enhanced superoxide anion production and decreased the availability of NO, suggesting that oxidative stress has been elevated. These results led authors to propose that inefficient metabolism in blood vessels causes atherosclerosis.

As already discussed above, atherosclerosis is a low-grade systemic inflammatory condition. One of the earliest signs of atherosclerosis is the development of abnormal mitochondria in smooth muscle cells (66), suggesting that mitochondrial dysfunction triggers the disease. The results of Bernal-Mizrachi et al (65) described above lend support to this view. Arteries have marginal oxygenation (67) and hypoxia reduces the respiratory control ratio (68). Uncoupled respiration precedes atherosclerosis at lesion-prone sites but not at the sites that are resistant to atherosclerosis (57). Disease-free aortae have abundant concentrations of the essential fatty acid-linoleate, whereas fatty streaks (an early stage of atherosclerosis) are deficient in EFAs (65, 69, 70). EFA deficiency promotes respiratory uncoupling (71, 72) and atherosclerosis (1, 73, 74). Bernal-Mizrachi et al showed that oxidative stress increases ROS generation and decreases NO formation and/or availability to be associated with smooth muscle expression of UCP-1. These results (65) and other studies (43-52) emphasize the importance of local disturbances of metabolism in the arterial wall are responsible for atherosclerosis and vascular disease, suggesting that strategies designed to revert to normal could prevent or postpone vascular diseases including CHD. In view of the many beneficial actions of EFAs and their products especially, with regard to their ability to enhance NO generation and regulate UCP expression increased intake of PUFAs may form one such approach.

Interaction(s) Between ω-3, ω-6 Fatty Acids, Trans-Fats, Saturated Fats, Cholesterol and its Relevance to Atherosclerosis Atherosclerotic plaque rupture is known to be responsible for sudden coronary events. Felton, et al. (75) reported that the concentrations of all fatty acids were increased at the edge of disrupted plaques compared with the center, but as a proportion of total fatty acids, ω-6 were lower. These results suggest that ω-6 fatty acids have a significant role in atherosclerosis and it is likely that some of the inconsistent results obtained in some studies with EPA and DHA could be attributed to inadequate provision or utilization of ω-6 fatty acids, especially DGLA and AA. It is possible that there is a close interaction between ω-3 and ω-6 fatty acids, which could influence one's susceptibility or resistance to atherosclerosis. In this context, it is interesting to note that EPA/DHA readily get incorporated into the atheromatous plaque, and patients treated with fish oil had more thick fibrous caps and no signs of inflammation compared with plaques in patients in the control and sunflower oil groups. Furthermore, the number of macrophages in plaques from patients receiving fish oil was lower than in the other two groups, suggesting that atherosclerotic plaques readily incorporate ω-3 PUFAs from fish-oil supplementation, inducing changes that can enhance stability of atherosclerotic plaques (76). In contrast, trans fatty acids may render atheromatous plaques unstable, partly by displacing ω-3 fatty acids, interfering with ω-3 fatty acid metabolism and activating inflammatory responses and endothelial dysfunction (77, 78). These results suggest that trans-fats not only enhance the risk of CAD (79, 80) but also induce plaque instability. In addition, trans-fats interfere with the activity of $\Delta^6$ and $\Delta^5$ desaturases (1, 7, 74, 81) that are essential for the conversion of dietary LA and ALA to their respective long-chain metabolites (see FIGS. 1-4). Thus, there is a close interaction between ω-3, ω-6 fatty acids and trans-fats.

In this context, the interaction between ω-3 and ω-6 fatty acids is particularly significant. In perfused vascular tissue, DGLA increases the conversion of EPA to $PGI_3$, a potent vasodilator and platelet anti-aggregator (82). In a similar fashion, AA augmented the conversion of EPA to $PGI_3$ in the tissues (83-85). On the other hand, EPA inhibits the activity of the enzyme $\Delta^5$ desaturase that results in an increase in the concentrations of DGLA in the tissues (especially in the endothelial cells). This increase in tissue levels of DGLA could enhance the formation of $PGE_1$, a vasodilator and platelet anti-aggregator, due to augmented precursor (DGLA) availability (see FIG. 4). Thus, EPA can indirectly enhance the formation of $PGE_1$. In contrast, trans-fats may interfere with the formation of DGLA, AA, EPA, and DHA from their respective dietary precursors by blocking the activity of $\Delta^6$ and $\Delta^5$ desaturases and thus, prevent the formation of useful and biologically active metabolites: $PGE_1$, $PGI_2$, $PGI_3$, LXs, resolvins and neuroprotectins and at the same time may augment the formation and/or action of LTs, and TXs. Thus, trans-fats could enhance the susceptibility of an individual to atheroma and CAD. Furthermore, even the beneficial action of statins (HMG-CoA reductase inhibitors) and glitazones (PPARs agonists) seem to be mediated by EFAs and their metabolites such as LXs, resolvins, and neuroprotectins (86-92), which are potent anti-inflammatory molecules (1, 93-95). On the other hand, cholesterol and saturated fatty acids similar to trans-fats block the activities of both $\Delta^6$ and $\Delta^5$ desaturases and inhibit the conversion of dietary LA and ALA to their respective long-chain metabolites and render cell membrane more rigid (1). Studies did suggest that increase in the consumption of trans-fats, cholesterol, and saturated fatty acids and increase in their plasma concentrations enhanced (96-98), whereas consumption of ω-3 fatty acids decreased the levels of inflammatory markers especially pro-inflammatory cytokines (99). These results imply that trans-fats, cholesterol, and saturated fatty acids have pro-inflammatory actions, while ω-3 fatty acids possess anti-inflammatory actions. The ability of trans-fats, saturated fatty acids and cholesterol to enhance plasma levels of pro-inflammatory cytokines may, in part, be due to their ability to suppress the production of ω-3 EPA and DHA since both EPA and DHA have been shown to inhibit T cell proliferation and their ability to produce IL-6 and TNF-α, which are pro-inflammatory cytokines (100, 101). This close interaction between ω-3 and ω-6 fatty acids, trans-fats, saturated fatty acids, cholesterol and their ability to modify inflammatory markers, production of $PGI_2$, $PGE_1$, $PGI_3$, LXs, resolvins, neuroprotectins, NO, nitrolipids, and the action of statins and glitazones on EFA metabolism and NO explains the relationship between various fatty acids, low-grade systemic inflammation, and their role in atheroma, CAD and stroke (FIGS. 4 and 5).

Mechanism(s) of the Atheroprotective Actions of ω-3 and ω-6 Fatty Acids

It is evident from the preceding discussion that both ω-3 and ω-6 PUFAs interact with each other to prevent atherosclerosis, CAD, CVD, and stroke, though ω-3 EPA and DHA seem to be having a more dominant role compared to ω-6 in this beneficial action. PUFAs display a multitude of actions to prevent atherosclerosis which are outlined below.

Effects on Plasma Lipids

In healthy subjects and patients with dyslipidemia, increased consumption of EPA and DHA, LA, GLA, and ALA is associated with falls in serum triglycerides and very low density lipoprotein, and when used at high doses both serum cholesterol and apolipoproteins B concentrations would also decrease (102-107). A tendency for the postprandial lipoprotein concentrations to fall was also noticed. In some instances either no change or a slight increase in the high-density lipoprotein cholesterol was reported. It is interesting that PUFAs are able to protect against the development of CAD, CVD, stroke, and atherosclerosis even though they do not dramatically increase HDL levels. This indicates that, hitherto, too much emphasis has been put on HDL levels by researchers in the prevention and treatment of CAD, CVD, stroke and atherosclerosis. For instance, in the GISSI study (108) patients who received ω-3 EPA and DHA did not show any significant changes in cholesterol (total, HDL, and LDL), blood glucose and fibrinogen concentrations compared with baseline values except for a small but significant decrease in triglyceride levels. This suggests that the effects on lipids do not seem to adequately explain the beneficial actions of EPA and DHA.

The hypotriglyceridemic effect of ω-3 fatty acids in humans seem to involve their action on liver X receptor, hepatocyte nuclear factor-4α(HNF-4α), farnesol X receptor, and peroxisome proliferator-activated receptors (PPARs) at the gene transcriptional level (Table 1). Each of these receptors is regulated by sterol receptor element binding protein-1c (SREBP-1c), the main genetic switch controlling lipogenesis. EPA/DHA coordinately suppress hepatic lipogenesis through reducing levels of SREBP-1c, upregulating fatty oxidation in the liver and skeletal muscle through PPAR activation and enhancing flux of glucose to glycogen through down regulation of HNF-4α. These actions result in the repartitioning of metabolic fuel from triglyceride storage toward oxidation, thereby reducing the substrate available for VLDL synthesis. By simultaneously downregulating genes encoding proteins that stimulate lipid synthesis and upregulating genes encoding proteins that stimulate fatty acid oxidation PUFAs reduce triglyceride levels. Furthermore, peroxidation of PUFAs reduce VLDL secretion through stimulating apolipoprotein B degradation, and enhances postprandial chylomicron clearance through reduced VLDL secretion and directly stimulates lipoprotein lipase activity-mechanisms by which PUFAs, especially ω-3 fatty acids, reduce postprandial hypertriglyceridemia (109).

Effects on Hemostatic System

Both EPA and DHA, when given orally, are rapidly incorporated into platelets and compete with AA for the 2-acyl position of membrane phospholipid and as substrate for the CO— and LO-enzymes. As a result, when stimulated such platelets produce less amounts of $TXA_2$ and more of $TXA_3$ that is less potent in inducing platelet aggregation and thrombosis (110). Inuit, who are on traditional diet, have a lower platelet count, less platelet aggregation, a longer bleeding time, higher urinary $PGI_2$ metabolites, and lower concentrations of thromboxane metabolites compared to those who were on Western diet (111, 112). Similar effects were found after an increase intake of fish or fish oil supplements that are rich in EPA/DHA (113, 114). But, no consistent effects on the prothrombin time, clotting factors, or anticoagulant proteins have been reported. Dietary supplementation with marine n-3 EPA/DHA fatty acids prolongs bleeding time and may decrease risk for thrombosis. Factor VII coagulant activity modestly decreases with reductions in saturated fatty acid (SFA) intake and thereby may contribute to the beneficial effects of low SFA diets. Large triglyceride-rich particles formed during postprandial lipemia can support the assembly and function of coagulation complexes and seem to play a role in the activation of factor VII, and thus may partially explain increased CVD risk associated with increased postprandial triglyceridemia. Increasing EPA/DHA intake and decreasing SFAs, trans-fats, and cholesterol may lead to reduce hemostatic CVD risk factors (115).

It is known that hypertriglyceridemia may represent a pro-coagulant state involving disturbances to the hemostatic system. Plasminogen activator inhibitor type 1 (PAI-1) is increased in the presence of hypertriglyceridemia. Free fatty acids (FFAs) in plasma may promote factor VII (FVII) activation. When the effect of different diets rich in various fatty acids such as stearic (S), palmitic (P), palmitic+myristic (M), oleic (O), trans 18:1 (T), and linoleic (L) acid were tested on the postprandial lipid and hemostatic profile (after 2, 4, 6, and 8 h) in young men, it was noted that all fats increased FVII activation. The stearic fat resulted in a lower increase in activated FVII (FVIIa) than did the trans fat and in a lower FVII coagulant activity (FVII:c) than did the oleic fat. When the data were pooled, the saturated fats resulted in a smaller postprandial increase in FVIIa, a smaller increase in FVII:c, a greater rise in tissue plasminogen activator concentrations, and a tendency to a greater postprandial decline in PAI-1 compared with the unsaturated fats, oleic acid, trans fat and LA. The increase in FVIIa was not significantly associated with the level of lipemia, plasma FFAs, or plasma lipoprotein lipase activity. These results indicate a lesser increase in FVIIa after the consumption of saturated fats, especially the stearic acid, than after unsaturated test fats (116). In a similar study wherein the first diet (high fat) rich in monounsaturated fatty acids (MUFA) and marine n-3 polyunsaturated fatty acids (PUFA), whereas the second diet (low-fat) was rich in complex carbohydrates and dietary fiber was used, it was observed that the high-fat diet induced a significant lowering of FIIc, FIXc, FXc, FVIIc, FVIIa, FXIIa, PAI-1, plasma viscosity, and platelet activity, but led to an increase in fibrinogen, whereas the low-fat diet lowered FXIIc values and induced a non-significant decrease in fibrinogen. However, as all changes appeared to be within the normal range of each hemostatic parameter, it is likely that the beneficial effects of the high-fat diet on most hemostatic factors are outweighed by the small increase in fibrinogen levels (117). These results emphasize the fact that the effects of fish oil and other lipids are more complex than simple enhancement or inhibition of fibrinolysis. Rather, the benefits may depend both on their concentration and whether they are present before or after the fibrin clots are formed. Thus, on the whole, though EPA and DHA do not seem to have a very significant effect on blood lipids, fibrinolysis and on the activity of PAI-1, still they are effective in preventing overall mortality from CAD/CVD. This apparently paradoxical beneficial action of EPA/DHA and ω-6 GLA, DGLA, and AA needs to be explained (81).

Effects on Endothelial Function

There is reasonable evidence to suggest that PUFAs, especially GLA, DGLA, AA, EPA, and DHA are necessary for endothelial health and normal function. It is obvious that endothelial cells should be able to produce adequate amounts of NO, $PGI_2$, $PGE_1$, LXs, and resolvins to prevent adhesion of platelets, leukocytes and macrophages to their surface that are known to produce ROS and pro-inflammatory cytokines and induce endothelial dysfunction. For endothelial cells to prevent platelet, leukocyte and macrophage adhesion and infiltration, they not only should be capable of producing adequate amounts of NO, $PGI_2$, $PGI_3$, LXs, and resolvins, but also suppress the expression of adhesion molecules on their surface and prevent the synthesis and release of IL-6, TNF-α, and MIF. EPA and DHA have been shown to reduce adhesion and migration of monocytes and inhibit leukocyte-endothelial cell interactions that involve increased endothelial expression of leukocyte adhesion molecules or endothelial activation (118-122). Several studies revealed that consumption of DHA/EPA reduced endothelial expression of vascular cell adhesion molecule-1 (VCAM-1), E-selectin, intercellular adhesion molecule-1 (ICAM-1), IL-6 and IL-8 in response to IL-1, IL-4, TNF-α, and bacterial endotoxin (118-122). When healthy human volunteers were given ω-3 PUFA (EPA and DHA) 6.6 g, ω-3 PUFA 2.0 g, or olive oil for 12 weeks in a double blind design, a significant decrease only in sP-selectin and a significant negative correlation was found between serum sICAM-1 levels and the DHA content of granulocyte membranes at entry that showed to be more marked in men. These results indicate that high-dose supplementation with ω-3 PUFA decreases sP-selectin levels in healthy subjects, thus suggesting a decrease in platelet reactivity or endothelial activation, though the effect of ω-3 PUFA on sCAMs is complex and may depend on gender and ω-3 PUFA dose (123). In another study, Johansen, et al (124) reported that ω-3 fatty acids decreased both tissue plasminogen activator antigen and soluble thrombomodulin, whereas in the placebo group soluble E-selectin and soluble VCAM-1 increased. These studies (118-124) suggest that ω-3 fatty acids decrease hemostatic markers of inflammation, show anti-inflammatory properties and inhibit endothelial activation.

Smooth muscle cell proliferation plays a significant role in the pathogenesis of atheroslcerosis and restenosis. Studies performed by Cornwell, et al (125, 126) revealed that both ω-3 and ω-6 fatty acids (especially AA, EPA, and DHA) do inhibit smooth muscle cell proliferation and that this is related to the amount of lipid peroxides formed in the cells. Several other investigators have confirmed these findings (127, 128). These studies imply that intracellular deficiency of PUFAs could lead to the initiation and progression of atherosclerosis and subsequent events. Pakala, et al (129) showed that smooth muscle cell proliferation induced by serotonin at the sites of vascular injury can be blocked by EPA and DHA, whereas Nakayama, et al (130) demonstrated that EPA inhibited TGF-β1 mRNA and cdk2 activity in vascular smooth muscle cells from spontaneously hypertensive rats. Others have confirmed these results (131, 132) suggesting that EPA and DHA, and possibly other PUFAs prevent endothelial activation, smooth muscle cell proliferation, and thus, prevent atheroslcerosis (133, 134).

Effects on Angiotensin-Converting Enzyme (ACE) and Endothelial Nitric Oxide

PUFAs inhibited leukocyte ACE activity (135, 136) suggesting that they could function as endogenous regulators of ACE activity, and thus regulate the formation of (angiotensin-II) Ang-II. PUFAs enhance endothelial NO generation (81, 137). Hence, when tissue/cell concentrations of PUFAs are low the formation of Ang-II will be high whereas that of eNO will be low. Plasma concentrations of PUFA and eNO are low in hypertension, diabetes mellitus, lupus, atherosclerosis, insulin resistance, and obesity (1, 2, 138, 139). Furthermore, a 25-nucleotide ACE deletion polymorphism increases ACE activity and such individuals showed a higher risk of developing stroke, obesity, emphysema, bipolar affective disorders, and cancers (140, 141). This suggests that an altered ACE activity and EFA metabolism plays a role in many diseases.

Transgenic rats overexpressing both human renin and angiotensinogen genes (dTGR) develop hypertension, inflammation, and renal failure and showed decreased formation epoxy-eicosatrienoic acids (5,6-, 8,9-, 11,12- and 14,15-EETs) and hydroxyeicosa-tetraenoic acids (19- and 20-HETEs) from AA. These EETs and HETEs inhibited IL-6 and TNF-α-induced activation of NF-κB and prevented vascular inflammation (142) suggesting that AA and other PUFAs not only regulate ACE activity and Ang-II levels but also possess anti-inflammatory properties.

EPA and AA stimulate eNO synthesis (1, 137). NO has potent anti-atherosclerotic and anti-inflammatory actions. Aspirin enhances the formation of eNO through the generation of epi-lipoxins that may explain its anti-inflammatory action (143). Epi-lipoxins that have potent anti-inflammatory actions enhance the generation of NO that, in turn, prevents the interaction between leukocytes and the vascular endothelium. NO stimulates the formation of $PGI_2$ from AA (144) and lipoxins are derived from AA, EPA, and DHA. Aspirin inhibits $TXA_2$ formation, a potent platelet aggregator and vasoconstrictor, and enhances $PGI_2$ formation, a platelet anti-aggregator and vasodilator, and thus brings about its anti-atherosclerotic actions. These results emphasize the close interaction between PUFAs, NO synthase, and COX enzymes (29).

Effects on Pro-Inflammatory Cytokines

ALA, DGLA, EPA, and DHA, LXs and resolvins suppress pro-inflammatory IL-1, IL-2, IL-6, macrophage migration inhibitory factor (MIF), HMGB1 (high mobility group box 1) and TNF-α production by T cells and other cells (1, 100, 101, 145, 146), and thus could function as endogenous anti-inflammatory molecules. $PGE_2$, $PGF_{2α}$, $TXA_2$ and LTs derived from AA also modulate IL-6 and TNF-α production. These results imply levels of IL-6 and TNF-α at the sites of inflammation and injury may depend on the local levels of various PUFAs and eicosanoids formed from them. In particular, the suppressive action of DHA on IL-1β and TNF-α production by stimulated human retinal vascular endothelial cells (147)

is interesting since this suggests that it (DHA) and possibly other PUFAs may be important to prevent atherosclerosis, macular degeneration, and diabetic retinopathy. The ability of EPA and DHA to suppress the production of pro-inflammatory cytokines and induce their anti-inflammatory actions are mediated by their ability to increase PPAR-γ mRNA and protein activity (148).

Effects on HMG-CoA Reductase Enzyme

The two sterol regulatory element-binding proteins (SREBPs): SREBP-1 and SREBP-2, each ~1150 amino acids in length, control the transcription of the genes for the low-density lipoprotein (LDL) receptor and 3-hydroxy-3-methyl-glutaryl coenzyme A (HMG-CoA) synthase. The proteolytic processing of both SREBPs is blocked by sterol overloading and enhanced when sterols are depleted by statins, the HMG-CoA synthesis inhibitors (149). Cholesterol depletion that occurs due to the use of statins leads to proteolytic activation of transcription factors of the SREBPs and also induces PPAR-γ expression (150), suggesting that PPAR-γ expression is controlled by SREBPs. Similar to statins, AA, EPA, and DHA are useful in the treatment of hyperlipidemias, have anti-proliferative action on tumor cells both in vitro and in vivo, bind to DNA and regulate the expression of genes and oncogenes. More importantly, PUFAs are also potent inhibitors of the HMG-CoA reductase enzyme (86, 151-153). Statins have the ability to enhance plasma AA concentrations and decrease the ratio of EPA to AA significantly. The beneficial actions of PUFAs in atherosclerosis can also be attributed to the formation of anti-inflammatory compounds such as lipoxins and resolvins.

PUFAs have inhibitory effects on SREBP-1a and SREBP-1c (154). In CaCo-2 cells, PUFAs decreased gene and protein expression of SREBP-1 and FAS mRNA by interfering with LXR activity (155), and in rats PUFAs enhanced cholesterol losses via bile acid synthesis (156). In the intestine, dietary PUFAs suppress SREBP-1c mRNA without altering expression of its target genes, fatty acid synthase, acetyl-CoA carboxylase, or ATP citrate lyase and decreased intestinal fatty acid synthesis by a posttranscriptional mechanism independent of the SREBP pathway (157). Feeding mice on fish oil diet for 2 weeks decreased serum cholesterol and triacylglycerol levels, by 50% and 60% respectively, hepatic FPP (farnesyl diphosphate synthase, a SREBP target enzyme that is subject to negative-feedback regulation by sterols in co-ordination with HMG-CoA reductase) synthase and HMG-CoA reductase mRNAs were decreased by 70% and 40% respectively. PUFAs down regulate hepatic cholesterol synthesis by impairing the SREBP pathway (158). PUFAs reduce SREBP-mediated gene transcription by increasing intracellular cholesterol content through the hydrolysis of cellular sphingomyelin, and the lipid second messenger ceramide, a product of sphingomyelin hydrolysis, decreased SRE-mediated gene transcription of SREBP-1 and SREBP-2 (159).

Thus, PUFAs (especially ω-3 EPA and DHA) inhibit ACE and HMG-CoA reductase activities and behave as endogenous ACE inhibitors and statins, suppress the production of pro-inflammatory cytokines, modulate SREBP pathway and thus, can inhibit atheroslcerosis both by lowering plasma triglycerides and cholesterol levels (see Table 1), and modulating inflammatory events.

$\Delta^6$ and $\Delta^5$ Desaturases as Biological Target(s) for the Prevention, Reversal, Arrest, and Treatment of Atherosclerosis It is evident from the preceding discussion that atherosclerosis can be revented/arrested if endothelial cells are able to produce adequate amounts of various PUFAs such that they in turn lead to the formation of beneficial $PGE_1$, $PGI_2$, $PGI_3$, LXs, resolvins, and nitrolipids that are capable of suppressing inflammation, expression of various adhesion molecules on the surface of endothelial cells, and prevent leukocyte, monocyte and macrophage infiltration of endothelial cells. For the production of adequate amounts of PUFAs to occur, endothelial cells should contain appropriate activities of $\Delta^6$ and $\Delta^5$ desaturases. In view of this, it is suggested that $\Delta^6$ and $\Delta^5$ desaturases could serve as biological target(s) for the prevention, arrest, reversal, and treatment of atherosclerosis.

Concept

EFAs/PUFAs are naturally occurring endogenous molecules that form precursors to several biologically active molecules such as $PGE_1$, $PGI_2$, $PGI_3$, lipoxins, resolvins, protectins, and form nitrolipids, and generate nitric oxide that prevent platelet aggregation, leukocyte activation, adherence of leukocytes and monocytes to endothelial cells and thus ultimately prevent, arrest, or even reverse atherosclerosis. The concentrations/levels of various EFAs/PUFAs such as GLA, DGLA, AA, EPA, and DHA could be enhanced in various cells and tissues especially, in endothelial cells by enhancing the activity of $\Delta^6$ and $\Delta^5$ desaturases that are essential for the conversion of dietary LA and ALA to their respective long-chain metabolites. In fact, there is evidence to suggest that activity of $\Delta^6$ and $\Delta^5$ desaturases is low in endothelial cells at the atheroslcerosis-prone areas of the vessels walls. This implies that a defect or deficiency of the activity of $\Delta^6$ and $\Delta^5$ desaturases is responsible for the initiation and progression of atheroslcerosis.

Based on these evidences, it is suggested that methods designed to enhance the activity of $\Delta^6$ and $\Delta^5$ desaturases forms a novel approach to prevent, arrest, reverse, and/or treat atherosclerosis. The activity of $\Delta^6$ and $\Delta^5$ desaturases can be enhanced by using proteins or peptides that show high affinity to these enzymes; lipids or lipoproteins that specifically bind to these enzymes to augment their activity; cDNAs of $\Delta^6$ and $\Delta^5$ desaturases can be incorporated into the endothelial cells or other types of cells (such that increased amounts of GLA, DGLA, AA, EPA, and DHA are formed that, in turn, get converted to $PGE_1$, $PGI_2$, $PGI_3$, lipoxins, resolvins, protectins, and enhance the formation of nitrolipids, and generate nitric oxide) that can be inserted or injected into the human body such that they home to the specific areas of blood vessels that are prone to atheroslcerosis so that further progression of atheroslcerosis can be arrested; lypopolysaccharides and other synthetic or naturally occurring substances can be used to enhance the activity of $\Delta^6$ and $\Delta^5$ desaturases: Synthetic analogues or structurally modified versions of various statins (HMG-CoA reductase inhibitors), folic acid, and troglitazones can also be used to enhance the activity of $\Delta^6$ and $\Delta^5$ desaturases for this purpose.

SUMMARY OF THE INVENTION

All the above factors and observations attest to the fact that the activity of $\Delta^6$ and $\Delta^5$ desaturases is crucial in the prevention and treatment of atheroslcerosis and in turn, conditions that are commonly associated with it such as obesity, type 2 diabetes mellitus, hypertension, CHD, and metabolic syndrome X, and Alzheimer's disease, depression, and other neurological conditions. In view of the significant role of various EFAs/PUFAs and their metabolites such as $PGE_1$, $PGI_2$, $PGI_3$, lipoxins, resolvins, protectins, nitrolipids, and nitric oxide in the prevention of atherosclerosis, several attempts have been made to enhance cell and tissue levels of EFAs/PUFAs. One such attempt is to provide orally or parentarally EFAs/PUFAs themselves with the hope that these fatty acids get incorporated into the endothelial cells and other cells and tissues and this may aid in the prevention and treatment of atherosclerosis. Although, provision of EFAs/PUFAs themselves directly to humans appears to be a simple and logical step to prevent and treat atheroslcerosis, there are some drawbacks to such an approach. For instance, what ever EFAs/PUFAs that are given orally need to be absorbed in sufficient amounts to get incorporated into endothelial cells to be effective; these fatty acids have to be provided daily; and despite all the advances in our understanding of the metabolism of EFAs/PUFAs still there is no consensus as to the correct dose and proportion in which these fatty acids have to be provided to humans. In view of these limitations of oral or even parentaral administration of EFAs/PUFAs, the present suggested method of directly stimulating the activity of $\Delta^6$ and $\Delta^5$ desaturases is the most appropriate course of action in our attempts to prevent and treat atherosclerosis. Such attempts to augment the activity of $\Delta^6$ and $\Delta^5$ desaturases directly in the cells and tissues and especially in endothelial cells will be more effective because it is expected that both $\Delta^6$ and $\Delta^5$ desaturases get activated by external stimuli only if their basal activity is low or sub-optimal. Hence, the likely danger of excess activity of $\Delta^6$ and $\Delta^5$ desaturases is unlikely.

The present invention specifically teaches that the efficacious use of various proteins, peptides, lipids, lipoproteins, glycolipids, synthetic chemicals such as statins and their derivatives, troglitazones and their derivatives, cDNA clones of $\Delta^6$ and $\Delta^5$ desaturases, genes of $\Delta^6$ and $\Delta^5$ desaturases, such that the cell and tissue especially, of endothelial cell content of various EFAs/PUFAs is enhanced and this, in turn, will lead to the prevention, arrest, reversal and treatment of atherosclerosis.

Described hereinafter is a novel method and approach to the prevention and treatment of atherosclerosis. Hitherto efforts have been made to arrest, prevent or treat atherosclerosis by enhancing plasma HDL (high-density lipoprotein) cholesterol, lowering LDL (low density lipoprotein) cholesterol and/or triglycerides that have not been very successful. On the other hand, the inventors noted to their surprise and unexpectedly that enhancing the activity of $\Delta^6$ and $\Delta^5$ desaturases arrested, prevented, and regressed very efficiently atherosclerosis even in the presence of low levels of HDL-cholesterol, high levels of LDL-cholesterol and high levels of triglycerides in the plasma. This indicates that even in the presence of adverse concentrations of plasma lipid profile, enhancing the activity of $\Delta^6$ and $\Delta^5$ desaturases efficiently prevented, arrested or regressed atherosclerosis in various blood vessels. In addition, it was noted that when the activity of $\Delta^6$ and $\Delta^5$ desaturases are enhanced the cell or tissue and plasma levels HDL-cholesterol increased marginally whereas the elevated levels of LDL-cholesterol and triglycerides became normal or fell dramatically. This indicates that increasing the cell or tissue activities of $\Delta^6$ and $\Delta^5$ desaturases reduces or normalized altered lipid profile without any adverse effects.

The objective of the invention is to provide a method or strategy of enhancing cell, and tissue levels of beneficial PUFAs by increasing the activities of $\Delta^6$ and $\Delta^5$ desaturases. Another objective of the invention is to provide a screening test system that can be used to evaluate various pharmacological preparation that are likely to enhance the activity of $\Delta^6$ and $\Delta^5$ desaturases. Such molecules either synthetic or natural compounds that could be screened for their effect on the activity of $\Delta^6$ and $\Delta^5$ desaturases may include: small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases to endothelial cells and other cells and tissues. The efficacy of such compounds on their ability to enhance the activity of $\Delta^6$ and $\Delta^5$ desaturases could be verified by measuring the formation of various types of PUFAs formed from labelled LA and ALA incorporated endothelial cells or other cells to study their (LA and ALA) conversion to their respective metabolites such as $PGE_1$, $PGI_2$, $PGI_3$, lipoxins, resolvins, protectins, GLA, DGLA, AA, EPA, and DHA, and other relevant products that indicate the presence/activity of $\Delta^6$ and $\Delta^5$ desaturases in the tested cells/tissues.

Administration of such identified small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases to endothelial cells and other cells and tissues could be made by any method, which allows the compound(s) to reach the site of desired action including endothelial cells and other cells including neuronal cells of the brain and endothelial cells of brain blood vessels. The compound(s) [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] can be administered orally in the form of dragees, tablets, syrups or ampules. When compounds [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] are administered rectally the composition can be in the form of a suppository. When the compounds [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] of the invention are to be administered by topical application for instance for various skin conditions, they can be in the form of pomade or a gel. Another example of preparation [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] can be as an intra-tumoral preparation in appropriate doses for the treatment of various neurological conditions such as depression, Alzheimer's disease, Parkinson's disease, Schizophrenia, etc. Another example of administration of the preparation [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] can be as selective intra-arterial infusion or injection into a specific artery that is feeding a specific region of the brain as desired by femoral, brachial or carotid routes or any other suitable route or in a combination with or without any other suitable agent. Further the compound(s) [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] can also be delivered using suitable devices, or a slow releasing capsule/tablet at an appropriate site or organ of the body. This preparation [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and A5 desaturases] can be administered daily, weekly, or monthly or at some other appropriate time of interval. Since the genes for $\Delta^6$ and $\Delta^5$ desaturases have been identified, cloned and expressed (160-168), it is possible to study the effects of various small molecules, and identify modulators of the activities of $\Delta^6$ and $\Delta^5$ desaturases in culture that could be used as a test system to know the efficacy of the compounds [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] administered on the activity of $\Delta^6$ and $\Delta^5$ desaturases in vitro. It is possible that such likely [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] can be selectively administered to the endothelial cells to prevent, arrest, reverse or treat existing atherosclerosis in coronary, cerebral and other blood vessels. Such administration of [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] to enhance the activity of $\Delta^6$ and $\Delta^5$ desaturases are also expected to be of benefit in the prevention and treatment of hyperlipidemia, hypertension, diabetes mellitus, and at sites of shear stress of blood flow, and insulin resistance, diseases that are also characterized by defective EFA metabolism, and mitochondrial dysfunction (65). Such compounds or molecules [small molecules, proteins, peptides, lipids, lipoproteins, glycolipids, synthetic chemicals such as statins and their derivatives, troglitazones and their derivatives, cDNA clones of $\Delta^6$ and $\Delta^5$ desaturases, and retroviral-directed (or by other means) delivery of genes for $\Delta^6$ and $\Delta^5$ desaturases] can also be used to prevent, reverse, or treat atherosclerosis in those subjects who have genetic polymorphism for $\Delta^6$ and $\Delta^5$ desaturases so that the severity and extent of atheroslcerosis in the carotid arteries, peripheral vascular tree, and coronary arteries can be arrested, reversed or treated efficiently.

Since PUFAs are naturally occurring endogenous substances, present in almost all tissues and are essential components of all mammalian cells it is likely that overexpression of $\Delta^6$ and $\Delta^5$ desaturases is not expected to have any significant side effects. This is evident form the fact that Eskimos consume large amounts of marine fish that are rich in ω-3 fatty acids EPA and DHA and are not known to suffer from any significant side effects. Similarly, when PUFAs have been administered to different types of patients for long periods of time (from few months to few years) it was noted that there were not any significant side effects.

Since $\Delta^6$ and $\Delta^5$ desaturases are present in many tissues, it is inferred that drugs or molecules that enhance the activities of $\Delta^6$ and $\Delta^5$ desaturases will have other beneficial actions such as in the treatment of hypertension, dyslipidemia, insulin resistance, diabetes mellitus, CHD, and CVD. Thus, increase in tissue/cell concentrations of PUFAs by increasing the activities of $\Delta^6$ and $\Delta^5$ desaturases is expected to have many beneficial actions.

Furthermore, it is also envisaged in this invention that the activities of the enzymes $\Delta^6$ and $\Delta^5$ desaturases may be used in the diagnosis of atherosclerosis, as a marker to know the response to treatment given to atherosclerosis, and as a prognostic marker of atherosclerosis.

BRIEF DESCRIPTION OF THE DRAWINGS

Essential fatty acids (EFAs) are important constituents of all cell membranes and alter membrane fluidity and thus, influence the activity of membrane-bound enzymes and receptors. EFAs are essential for humans and as are not synthesized in the body; have to be obtained in the diet (1). The two EFAs are ω-6 cis-linoleic acid (LA, 18:2) and the ω-3 α-linolenic acid (ALA, 18:3). LA is converted to γ-linolenic acid (GLA, 18:3, n-6) by the enzyme $\Delta^6$ desaturase and GLA is elongated to form dihomo-GLA (DGLA, 20:3, ω-6), the precursor of the 1 series of prostaglandins (PGs). DGLA can also be converted to arachidonic acid (AA, 20:4, ω-6) by the enzyme $\Delta^5$ desaturase. AA forms the precursor of 2 series of PGs, TXs and the 4 series of LTs. ALA is converted to EPA (20:5, ω-3) by $\Delta^6$ and $\Delta^5$ desaturases. EPA forms the precursor of the 3 series of PGs, TXs and the 5 series of LTs. LA, GLA, DGLA, AA, ALA, EPA and DHA (22:6, ω-3) are all PUFAs, but only LA and ALA are EFAs (see FIGS. 1-3 for metabolism of EFAs). AA and EPA also are converted to their respective LTs. PGs, TXs, and LTs, which play an important role in atherosclerosis, CHD, bronchial asthma, inflammatory bowel disease, and other inflammatory conditions (1).

Atherosclerotic plaque rupture is known to be responsible for sudden coronary events. It is known that the concentrations of all fatty acids were increased at the edge of disrupted plaques compared with the center, but as a proportion of total fatty acids, ω-6 was lower, suggesting that ω-6 fatty acids have a significant role in atherosclerosis. This also suggests that to some extent EPA and DHA need ω-6 fatty acids, especially DGLA and AA to produce some of their beneficial actions, implying a close interaction between ω-3 and ω-6 fatty acids, which could influence one's susceptibility or resistance to atherosclerosis. It is interesting to note that EPA/DHA readily get incorporated into the atheromatous plaque, and patients treated with fish oil had more thick fibrous caps and no signs of inflammation compared with plaques in patients in the control and sunflower oil groups. The number of macrophages in plaques from patients receiving fish oil was lower than in the other two groups, suggesting that ω-3 PUFAs from fish-oil supplementation enhance stability of atherosclerotic plaques (76). In contrast, trans-fatty acids render atheromatous plaques unstable, partly by displacing ω-3 fatty acids, interfering with ω-3 fatty acid metabolism and activating inflammatory responses and endothelial dysfunction (77, 78). These results suggest that trans-fats not only enhance the risk of CAD (79, 80) but also induce plaque instability. In addition, trans-fats interfere with the activity of $\Delta^6$ and $\Delta^5$ desaturases (1, 7, 74, 81) that are essential for the conversion of dietary LA and ALA to their respective long-chain metabolites (see FIGS. 1-4). Thus, there is a close interaction between ω-3, ω-6 fatty acids and trans-fats.

In this context, the interaction between ω-3 and ω-6 fatty acids is particularly significant. It is known that DGLA increases the conversion of EPA to $PGI_3$, a potent vasodilator and platelet anti-aggregator (82). In a similar fashion, AA augmented the conversion of EPA to $PGI_3$ in the tissues (83-85). On the other hand, EPA inhibits the activity of the enzyme $\Delta^5$ desaturase that results in an increase in the concentrations of DGLA in the tissues (especially in the endothelial cells). This increase in tissue levels of DGLA could enhance the formation of $PGE_1$, a vasodilator and platelet anti-aggregator, due to augmented precursor (DGLA) availability (see FIG. 4). Thus, EPA can indirectly enhance the formation of $PGE_1$. In contrast, trans-fats interfere with the formation of DGLA, AA, EPA, and DHA from their respective dietary precursors by blocking the activity of $\Delta^6$ and $\Delta^5$ desaturases and thus, prevent the formation of useful and biologically active metabolites: $PGE_1$, $PGI_2$, $PGI_3$, LXs, resolvins and neuroprotectins and at the same time may augment the formation and/or action of LTs, and TXs. Thus, trans-fats could enhance the susceptibility of an individual to atheroma and CAD. Even statins (HMG-CoA reductase inhibitors) and glitazones (PPARs agonists) have been shown to enhance the metabolism of EFAs and the formation of LXs, resolvins, and neuroprotectins (86-92), which are potent anti-inflammatory molecules (1, 93-95) and thus, bring about their beneficial actions. On the other hand, cholesterol and saturated fatty acids similar to trans-fats block the activities of both $\Delta^6$ and $\Delta^5$ desaturases and inhibit the conversion of dietary LA and ALA to their respective long-chain metabolites (1). Studies did suggest that increase in the consumption of trans-fats, cholesterol, and saturated fatty acids and increase in their plasma concentrations enhanced (96-98), whereas consumption of ω-3 fatty acids decreased the levels of inflammatory markers especially pro-inflammatory cytokines (99). Thus, trans-fats, cholesterol, and saturated fatty acids have pro-inflammatory actions, while ω-3 fatty acids possess anti-inflammatory actions. This close interaction between ω-3 and ω-6 fatty acids, trans-fats, saturated fatty acids, cholesterol and their ability to modify inflammatory markers, production of $PGI_2$, $PGE_1$, $PGI_3$, LXs, resolvins, neuroprotectins, NO, nitrolipids, and the action of statins and glitazones on EFA metabolism and NO explains the relationship between various fatty acids, low-grade systemic inflammation, and their role in atheroma, CAD and stroke (FIGS. 4 and 5).

DETAILED DESCRIPTION

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference.

DEFINITIONS

In order to more clearly and concisely describe the subject matter which is the invention, the following definitions are provided for certain terms which are used in the specification and appended claims.

As used herein, the term atherosclerosis refers to a disease of the arterial wall in which the layer thickens, causing narrowing of the channel and thus, impairing blood flow. It can occur in any area of the body, but is most important when it happens in the heart, brain or blood vessels leading to the brain. The narrowing is due to the formation of plaques (raised patches) in the inner lining of the arteries. These plaques consist of low-density lipoproteins, decaying muscle cells, fibrous tissue, clumps of blood platelets, cholesterol, and sometimes calcium. They tend to form in regions of turbulent blood flow and are found most often in people with high concentrations of cholesterol in the bloodstream. The number and thickness of plaques increases with age, causing loss of the smooth lining of the blood vessels and encouraging the formation of thrombi (blood clots). Sometimes fragments of thrombi break off and form emboli, which travel through the bloodstream and block smaller vessels.

Atherosclerosis is responsible for more deaths in the U.S. than any other condition. Atherosclerotic heart disease, involving the coronary arteries (also called as coronary heart disease), is the most common cause of death, accounting for one-third of all deaths. Atherosclerotic interference with blood supply to the brain causes stroke that is the third most common cause of death after cancer. Atherosclerosis also causes a great deal of serious illness by reducing the flow of blood in other major arteries, such as to the kidneys, legs, and intestines.

Why does atherosclerosis occur in the coronary arteries of some people but not others is not known. An interplay of many factors including hypertension (high blood pressure), smoking, diabetes, obesity, high cholesterol, family history of heart disease, and a sedentary lifestyle are involved have been blamed for the occurrence of atherosclerosis.

The present invention suggests that the cause of atherosclerosis is due to the defect in the activities of enzymes $\Delta^6$ and $\Delta^5$ desaturases. It is also the purpose of this invention to propose that enhancement of the activities of the enzymes $\Delta^6$ and $\Delta^5$ desaturases prevents, reverses, arrests, and could be used as a strategy to treat atherosclerosis. Furthermore, it is suggested that those who have a defect in the activities of the enzymes $\Delta^6$ and $\Delta^5$ desaturases are more prone to develop atherosclerosis compared to those who have normal activities of the enzymes $\Delta^6$ and $\Delta^5$ desaturases. Thus, susceptibility or resistance to develop atherosclerosis is dependent on the activities of the enzymes $\Delta^6$ and $\Delta^5$ desaturases especially in the endothelial cells of the vessel walls. Hence, strategies that increase the activities of the enzymes $\Delta^6$ and $\Delta^5$ desaturases in the endothelial cells of vessel walls will not only prevent, reverse, and/or arrest atherosclerosis but also can be used as a treatment option in those who already have atherosclerosis.

As used herein, the term "polyunsaturated fatty acid" and the abbreviation "PUFA" mean any acid derived from fats by hydrolysis, or any long-chain (at least 12 carbons) organic acid, having at least two carbon-to-carbon double bonds. Examples of PUFAs include but are not limited to linoleic acid, linolenic acid and arachidonic acid.

As used herein, the term "PUFA salt" means an ionic association, in solid or in solution, of a anionic form of a PUFA with a cation of a small organic group (e.g., ammonium) or a small inorganic group (e.g., an alkali metal). Preferred salts are those between a PUFA and an alkali metal (e.g., lithium, sodium, potassium), an alkali earth metal (e.g., magnesium, calcium) or a multivalent transition metal (e.g., manganese, iron, copper, aluminum, zinc, chromium, cobalt, nickel).

General Considerations

The present invention is dependent, in part, upon the discovery of the novel and highly beneficial action of PUFAs to inhibit the proliferation of smooth muscle cells of the vessel walls, maintain the integrity and health of endothelial cells lining the vessel walls, and consequently enhance the ability of endothelial cells to produce adequate amounts of anti-atherosclerotic molecules such as prostaglandin $E_1$ ($PGE_1$), prostacyclin ($PGI_2$), prostaglandin $I_3$ ($PGI_3$), resolvins, lipoxins, and protectins, and nitrolipids form their respective precursors. For the production of these anti-atherosclerotic molecules in adequate amounts from their precursors normal and adequate activity of the enzymes $\Delta^6$ and $\Delta^5$ desaturases is essential.

Without being bound to any particular theory of the invention, it is believed that the selective enhancement of the activity of enzymes $\Delta^6$ and $\Delta^5$ desaturases will inhibit the proliferation of smooth muscle cells of the vessel walls, enhance the integrity and survival of endothelial cells of the vessel walls, and augment their (endothelial cells) ability to produce the various anti-atherosclerotic molecules such as prostaglandin $E_1$ ($PGE_1$), prostacyclin ($PGI_2$), prostaglandin $I_3$ ($PGI_3$), resolvins, lipoxins, and protectins, and nitrolipids from their precursors PUFAs (for metabolism of essential fatty acids see FIGS. 1-4). This beneficial action due to the selective enhancement of the activity of enzymes $\Delta^6$ and $\Delta^5$ desaturases is due to the formation of various PUFAs in adequate amounts in the endothelial cells of the vessel walls and these PUFAs, in turn, are utilized to form various anti-atherosclerotic molecules such as prostaglandin $E_1$ ($PGE_1$), prostacyclin ($PGI_2$), prostaglandin $I_3$ ($PGI_3$), resolvins, lipoxins, and protectins, and nitrolipids. As a result, various diseases that occur as a consequence of atherosclerosis such as coronary heart disease, stroke, and reduced flow of blood to other major arteries, such as to the kidneys, legs, and intestines would not occur (see FIG. 5 for the relationship between $\Delta^6$ and $\Delta^5$ desaturases, PUFAs and their products and various diseases).

This conclusion follows from observations in several patients that normalcy is restored when the activities of the enzymes $\Delta^6$ and $\Delta^5$ desaturases was enhanced or restored to normal as outlined in the present invention.

Finally, without being bound to any particular theory of the invention, it is believed that enhancement of the activities of the enzymes $\Delta^6$ and $\Delta^5$ desaturases in endothelial cells of the vessel walls accounts for the effectiveness of the treatment even compared to administration of PUFAs themselves. Thus, the therapeutic effect produced by enhancing the activities of the enzymes $\Delta^6$ and $\Delta^5$ desaturases in the endothelial cells of the vessel walls is qualitatively different than the effect that is obtained by the administration of PUFAs themselves.

There are several advantages of activating the action of the enzymes $\Delta^6$ and $\Delta^5$ desaturases in the endothelial cells of the vessel walls. In each of the embodiments described here, the enzymes $\Delta^6$ and $\Delta^5$ desaturases are activated or delivered to the endothelial cells of the vessel walls preferably in the form of proteins, peptides, lipids, lipoproteins, glycolipids, synthetic chemicals such as statins and their derivatives, troglitazones and their derivatives, and other compounds (synthetic or natural) that have the ability to enhance the activities of $\Delta^6$ and $\Delta^5$ desaturases. The invention also provides methods of efficiently delivering cDNA clones of $\Delta^6$ and $\Delta^5$ desaturases and genes of $\Delta^6$ and $\Delta^5$ desaturases to endothelial cells and other target cells and tissues to prevent, arrest, reverse and treat atherosclerosis. Efficient delivery of cDNA clones of $\Delta^6$ and $\Delta^5$ desaturases and genes of $\Delta^6$ and $\Delta^5$ desaturases to endothelial cells can also be achieved by delivering cDNA clones and genes of $\Delta^6$ and $\Delta^5$ desaturases as nano particles and using liposomal techniques. Selective delivery of enzymes $\Delta^6$ and $\Delta^5$ desaturases to endothelial cells can be achieved by injecting the said cDNA clones, genes of the enzymes $\Delta^6$ and $\Delta^5$ desaturases into the selected area of endothelial cells of a specific blood vessel such as coronary artery, cerebral artery or any peripheral artery of the body without affecting normal tissue cells by using a hollow core needle that can be inserted into the body, the needle being visually guided by a selected imaging technique. Such specific injection and thus, delivery of enzymes $\Delta^6$ and $\Delta^5$ desaturases to endothelial cells can be achieved by utilizes an endoscopic instrument, wherein a probe is inserted into the body, guided by the endoscope to the vicinity of the target area. The hollow core needle is guided to the vicinity by a channel through the probe. A needle adjustment apparatus is used to extend or retract the needle and adjust needle tip orientation toward a target area. The endoscope provides a view to an operator for adjustment of the apparatus to extend the tip of the needle into and through tissue, interstitially, to a target area for deposit of the specific treatment fluid. A non-invasive imaging technique is used either alone, or in addition to the endoscope, to give an operator a view of the needle for guiding the needle tip to the precise target area. Typical non-invasive techniques include CT scan, MRI, ultrasound etc.

Methods of Administration

The method of delivery of the cDNA clones, liposomes, nanoparticles containing enzymes $\Delta^6$ and $\Delta^5$ desaturases are preferably administered orally, intravenously, intramuscularly, subcutaneously, intra-arterially to an artery which is close to the site of the disease or using specialized equipment through endoscopic devices. When the cDNA clones, liposomes or nanoparticles containing either the DNA sequences of $\Delta^6$ and $\Delta^5$ desaturases or pure enzymes $\Delta^6$ and $\Delta^5$ desaturases are given orally they are administered in such a way that the enzymes or the DNA sequences are not inactivated by the acid or enzymes present in the stomach and duodenum by coating the cDNA sequences, nano particles, and liposomes with suitable substances such that ultimately $\Delta^6$ and $\Delta^5$ desaturases are delivered to the endothelial cells of the vessel walls intact and in an active form to produce their actions.

Appropriate dosages of the cDNA sequences, nano particles, and liposomes containing $\Delta^6$ and $\Delta^5$ desaturases depend primarily on the severity and stage of the disease, and the various areas of the vessel walls where they need to be delivered and act. Preferred dosages range from approximately 0.5 ng (nano grams) to 500 gm of cDNA sequences, nano particles, and liposomes with suitable pharmaceutical delivery systems is used such that ultimately $\Delta^6$ and $\Delta^5$ desaturases are delivered in adequate amounts to the endothelial cells of the vessel walls.

Other Agents

The cDNA sequences, nano particles, and liposomes containing $\Delta^6$ and $\Delta^5$ desaturases may be administered alone, or in combination with other pharmaceutical agents known to be useful in the treatment of atherosclerosis known to those skilled in the art. Thus, for example, cDNA sequences, nano particles, and liposomes containing $\Delta^6$ and $\Delta^5$ desaturases may be co-administered with known anti-diabetic drugs including tolbutamide, phenformin, metformin, glibenclamide, insulin, glitazones, DPP-4 inhibitors (dipeptidyl peptidase-4 inhibitor) such as vildagliptin, sitagliptin, saxagliptin, anti-hypertensive drugs, drugs used for the treatment of coronary heart disease, stroke, and peripheral vascular disease.

Administration of these agents in combination with cDNA sequences, nano particles, and liposomes containing $\Delta^6$ and $\Delta^5$ desaturases, or PUFAs may also show a synergistic or potentiating effect.

Thus, in another aspect, the invention provides pharmaceutical compositions comprising a cDNA sequences, nano particles, and liposomes containing $\Delta^6$ and $\Delta^5$ desaturases, PUFAs and a pharmaceutical agent known in the art for the treatment of obesity, diabetes mellitus, metabolic syndrome X, depression, dementia, Alzheimer's disease, Parkinson's disease, either in solution, or in an emulsion. The cDNA sequences, nano particles, and liposomes containing $\Delta^6$ and $\Delta^5$ desaturases, PUFAs and other pharmaceutical agent may be separate chemical moieties combined in the solution or emulsion, or they may be covalently conjugated. The preferred pharmaceutical agents are as disclosed above.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the appended claims.

Although the invention is described primarily as it relates to humans, it is envisaged that the methods of the invention are equally applicable to other mammals, including large domesticated mammals (e.g., race horses, breeding cattle) and smaller domesticated animals (e.g., house pets).

REFERENCES

1. Das U N. Essential fatty acids: Biochemistry, physiology and pathology. *Biotech J* 2006; 1: 420-439.
2. Das U N. Essential fatty acid metabolism in patients with essential hypertension, diabetes mellitus and coronary heart disease. *Prostaglandins Leukotrienes Essential Fatty Acids* 1995; 52: 387-391.
3. Kumar K V and Das U N. Lipid peroxides and essential fatty acids in patients with coronary heart disease. *J Nutritional Med* 1994; 4: 33-37.
4. Das U N. Nutritional factors in the pathobiology of human essential hypertension. *Nutrition* 2001; 17: 337-346.
5. Das U N. Can perinatal supplementation of long chain polyunsaturated fatty acids prevent hypertension in adult life? *Hypertension* 2001; 38: e6-e8.
6. Das U N. Can perinatal supplementation of long-chain polyunsaturated fatty acids prevent diabetes mellitus? *Eur J Clin Nutrition* 2003; 57: 218-226.
7. Das U N. A defect in the activity of $\Delta^6$ and $\Delta^5$ desaturases may be a factor predisposing to the development of insulin resistance syndrome. *Prostaglandins Leukotrienes Essen Fatty Acids* 2005; 72: 343-350.
8. Wang L, Folsom A R, Eckfeldt J H. Plasma fatty acid composition and Incidence of coronary heart disease in middle aged adults: the Atherosclerosis Risk in Communities (ARIC) Study. *Nutr Metab Cardiovasc Dis* 2003; 13: 256-66.
9. Zheng Z J, Folsom A R, Ma J, Arnett D K, McGovern P G, Eckfeldt J H. Plasma fatty acid composition and 6-year incidence of hypertension in middle-aged adults: the Atherosclerosis Risk in Communities (ARIC) Study. *Am J Epidemiol* 1999; 150: 492-500.
10. Suresh Y and Das U N. Differential effect of saturated, monounsaturated, and polyunsaturated fatty acids on alloxan-induced diabetes mellitus. *Prostaglandins Leukot Essen Fatty Acids* 2006; 74: 199-213.
11. Suresh Y and Das U N. Long-chain polyunsaturated fatty acids and chemically-induced diabetes mellitus: Effect of ω-6 fatty acids. Nutrition 2003; 19: 93-114.
12. Suresh Y, Das U N. Long-chain polyunsaturated fatty acids and chemically-induced diabetes mellitus: Effect of ω-3 fatty acids. *Nutrition* 2003; 19: 213-228.
13. Mozaffarian D, Ascherio A, Hu F B, Stampfer M J, Willett W C, Siscovick D S, Rimm E B. Interplay between different polyunsaturated fatty acids and risk of coronary heart disease in men. *Circulation* 2005; 111: 157-164.
14. Das U N. Clinical laboratory tools to diagnose inflammation. *Adv Clin Chem* 2006; 41: 189-229.
15. Brennan M L, Penn M S, Lente F V, Nambi V, Shishehbor M H, Aviles R J, Goormastic M, Pepoy M L, McErlean E S, Topol E J, Nissen S E, Hazen S L. Prognostic value of myeloperoxidase in patients with chest pain. *N Engl J Med* 2003; 349: 1595-1604.
16. Ballantyne C M, Hoogeveen R C, Bang H, Coresh J, Folsom A R, Heiss G, Sharrett A R. Lipoprotein-associated phospholipase $A_2$, high-sensitivity C-reactive protein, and risk for incident coronary heart disease in middle-aged men and women in the Atherosclerosis Risk in Communities (ARIC) Study. *Circulation* 2004; 109: 837-842.
17. Oei H H S, van der Meer I M, Hofman A, Koudstaal P J, Stijnen T, Breteler M M B, Witteman J C M. Lipoprotein-associated phospholipase $A_2$ activity is associated with risk of coronary heart disease and ischemic stroke. The Rotterdam study. *Circulation* 2005; 111: 570-575.
18. Loffredo L, Pignatelli P, Cangemi R, Andreozzi P, Panico M A, Meloni V, Violi F. Imbalance between nitric oxide generation and oxidative stress in patients with peripheral arterial disease: effect of an antioxidant treatment. *J Vasc Surg* 2006; 44: 525-530.
19. Aygul R, Kotan D, Demirbas F, Ulvi H, Deniz O. Plasma oxidants and antioxidants in acute ischaemic stroke. *J Int Med Res* 2006; 34: 413-418.
20. Collino M, Aragno M, Mastrocola R, Gallicchio M, Rosa A C, Dianzani C, Danni O, Thiemermann C, Fantozzi R. Modulation of the oxidative stress and inflammatory response by PPAR-gamma agonists in the hippocampus of rats exposed to cerebral ischemia/reperfusion. *Eur J Pharmacol* 2006; 530: 70-80.
21. Kumar K V and Das U N. Lipid peroxides and essential fatty acids in patients with coronary heart disease. *J Nutritional Med* 1994; 4: 33-37.
22. Das U N. Free radicals, cytokines and nitric oxide in cardiac failure and myocardial infarction. *Mol Cell Biochem* 2000; 215: 145-152.
23. Kumar V, Abbas A K, Fausto N. Acute and chronic inflammation. In: Robbins and Cotran Pathologic Basis of Disease, Elsevier Saunders, 7th edition, 2005, pp. 47-86.
24. Claria J, Serhan C N. Aspirin triggers previously undescribed bioactive eicosanoids by human endothelial cell-leukocyte interactions. *Proc Natl Acad Sci USA* 1995; 92: 9475-9479.
24. Mozaffarian D, Pischon T, Hankinson S E, Rifai N, Joshipura K, Willett W C, Rimm E B. Dietary intake of trans fatty acids and systemic inflammation in women. *Am J Clin Nutr* 2004; 79: 606-612.
26. Brenner R R. Nutritional and hormonal factors influencing desaturation of essential fatty acids. *Prog Lipid Res* 1982; 20: 41-48.
27. Matsuzaka T, Shimano H, Yahagi N, Amemiya-Kudo M, Yoshikawa T, Hasty A H, Tamura Y, Osuga J, Okazaki H, Iizuka Y, Takahashi A, Sone H, Gotoda T, Ishibashi S, Yamada N. Dual regulation of mouse Delta(5)- and Delta(6)-desaturase gene expression by SREBP-1 and PPARalpha. *J Lipid Res* 2002; 43: 107-114.
28. Cook H W. The influence of trans acids on desaturation and elongation of fatty acids. *Lipids* 1981; 16: 920-926.
29. Das U N. COX-2 inhibitors and metabolism of essential fatty acids. *Med Sci Monit* 2005; 11: RA233-RA237.
30. Serhan C N, Clish C B, Brannon J, Colgan S P, Chiang N, Gronert K. Novel functional sets of lipid-derived mediators with antiinflammatory actions generated from omega-3 fatty acids via cyclooxygenase 2-nonsteroidal antiinflammatory drugs and transcellular processing. *J Exp Med* 2000; 192: 1197-1204.
31. Serhan C N, Hong S, Gronert K, Colgan S P, Devchand P R, Mirick G, Moussignac R-L. Resolvins: A family of bioactive products of omega-3 fatty acid transformation circuits initiated by aspirin treatment that counter proinflammation signals. *J Exp Med* 2002; 196: 1025-1037.
32. Levy B D, Clish C B, Schmidt B, Gronert K, Serhan C N. Lipid mediator class switching during acute inflammation signals in resolution. *Nat Immunol* 2001; 2: 612-619.
33. Hong S, Gronert K, Devchand P R, Moussignac R L, Serhan C N. Novel docosatrienes and 17S-resolvins generated from docosahexaenoic acid in murine brain, human blood, and glial cells. Autacoids in anti-inflammation. *J Biol Chem* 2003; 278: 14677-14687.
34. Marcheselli V L, Hong S, Lukiw W J, Tian X H, Gronet K, Musto A, Hardy M, Gimenez J M, Chiang N, Serhan C N, Bazan N G. Novel docosanoids inhibit brain ischemia-reperfusion-mediated leukocyte infiltration and pro-inflammatory gene expression. *J Biol Chem* 2003; 278: 43807-43817.
35. Mukherjee P K, Marcheselli V L, Serhan C N, Bazan N G. Neuroprotectin D1: a docosahexaenoic acid-derived docosatriene protects human retinal pigment epithelial cells from oxidative stress. *Proc Natl Acad Sci USA* 2004; 101: 8491-8496.
36. Gronert K, Maheshwari N, Khan N, Hasan I R, Dunn M, Laniado Schwartzman M. A role for the mouse 12/15-lipoxygenase pathway in promoting epithelial wound healing and host defense. *J Biol Chem* 2005; 280: 15267-15278.
37. Lukiw W J, Cui J-G, Marcheselli V L, Bodker M, Botkjaer A, Gotlinger K, Serhan C N, Bazan N G. A role for docosahexaenoic acid-derived neuroprotectin D1 in neural cell survival and Alzheimer disease. *J Clin Invest* 2005; 115: 2774-2783.
38. Calon F, Lim G P, Morihara T, Yang F, Ubeda O, Salem N Jr, Frautschy S A, Cole G M. Dietary n-3 polyunsaturated fatty acid depletion activates caspases and decreases NMDA receptors in the brain of a transgenic mouse model of Alzheimer's. *Eur J Neurosci* 2005; 22: 617-626.
39. Baker P R S, Lin Y, Schopfer F J, Woodcock S R, Groeger A L, Batthyany C, Swooney S, Long M H, Iles K E, Baker L M S, Branchaud B P, Chen Y, Freeman B A. Fatty acid transduction of nitric oxide signaling: Multiple nitrated unsaturated fatty acid derivatives exist in human blood and urine and serve as endogenous peroxisome proliferator-activated receptor ligands. *J Biol Chem* 2005; 280: 42464-42475.
40. Coles B, Bloodsworth A, Clark S R, Lewis M J, Cross A R, Freeman B A, O'Donnell V B. Nitrolinoleate inhibits superoxide generation, degranulation, and integrin expression by human neutrophils. *Circ Res* 2002; 91: 375-381.
41. Lima E S, Bonim M G, Augusto O, Barbeiro H V, Souza H P, Abdalla D S P. Nitrated lipids decompose to nitric oxide and lipid radicals and cause vasorelaxation. *Free Radic Biol Med* 2005; 39: 532-539.
42. Danesh J, Collins R, Appleby P, Peto R. Association of fibrinogen, C-reactive protein, albumin, or leukocyte count with coronary heart disease: meta-analyses of prospective studies. *JAMA* 1998; 279: 1477-1482.
43. Brooks A R, Lelkes P I, Rubanyi G M. Gene expression profiling of human aortic endothelial cells exposed to disturbed flow and steady laminar flow. *Physiol Genomics* 2002; 9: 27-41.
44. Garcia-Cardena G, Comander J, Anderson K R, Blackman B R, Gimbrone M A Jr. Biomechanical activation of vascular endothelium as a determinant of its functional phenotype. *Proc Natl Acad Sci USA* 2001; 98: 4478-4485.
45. Gimbrone M A Jr, Nagel T, Topper J N. Biomechanical activation: an emerging paradigm in endothelial adhesion biology. *J Clin Invest* 1997; 100: S61-S65.
46. Hajra L, Evans A I, Chen M, Hyduk S J, Collins T, Cybulsky M I. The NF-kappa B signal transduction pathway in aortic endothelial cells is primed for activation in regions predisposed to atherosclerotic lesion formation. *Proc Natl Acad Sci USA* 2000; 97: 9052-9057.
47. Nakashima Y, Raines E W, Plump A S, Breslow J L, Ross R. Upregulation of CAM-1 and ICAM-1 at atheroslcerosis-prone sites on the endothelium in the ApoE-deficient mouse. *Arterioscler Thromb Vasc Biol* 1998; 18: 842-851.
48. Iiyama K, Hajra L, Iiyama M, Li H, DiChiara M, Medoff B D, Cybulsky M I. Patterns of vascular cell adhesion molecule-1 and intercellular adhesion molecule-1 expression in rabbit and mouse atheroslcerotic lesions and at sites predisposed to lesion formation. *Circ Res* 1999; 85: 199-207.
49. Passerini A G, Polacek D C, Shi C, Francesco N M, Manduchi E, Grant G R, Pritchard W F, Powell S, Chang G Y, Stoeckert C J Jr, Davies P F. Coexisting proinflammatory and antioxidative endothelial transcription profiles in a disturbed flow region of the adult porcine aorta. *Proc Natl Acad Sci USA* 2004; 101: 2482-2487.
50. Schwenke D C, Carew T E. Initiation of atheroslcerotic lesions in cholesterol-fed rabbits. I. Focal increases in arterial LDL concentration precede development of fatty streak lesions. *Arteriosclerosis* 1989; 9: 895-907.
51. Schwenke D C, Carew T E. Initiation of atherosclerotic lesions in cholesterol-fed rabbits. II. Selective retention of LDL vs. selective increases in LDL permeability in susceptible sites of arteries. *Arteriosclerosis* 1989; 9: 908-918.
52. Schwenke D C. Selective increase in cholesterol at atherosclerosis-susceptible aortic sites after short-term cholesterol feeding. *Arterioscler Throm Vasc Biol* 1995; 15: 1928-1937.
53. Napoli C, D'Armiento F P, Mancini F P, Postiglione A, Witzturn J L, Palumbo G, Palinski W. Fatty streak formation occurs in human fetal aortas and is greatly enhanced by maternal hypercholesterolemia. Intimal accumulation of low density lipoprotein and its oxidation precede monocytic recruitment into early atherosclerotic lesions. *J Clin Invest* 1997; 100: 2680-2690.
54. Shi W, Haberland M E, Jien M L, Shih D M, Lusis A J. Endothelial responses to oxidized lipoproteins determine genetic susceptibility to atherosclerosis in mice. *Circulation* 2000; 102: 75-81.
55. Cybulsky M I, Won D, Haidari M. Leukocyte recruitment to atherosclerotic lesion. *Can J Cardiol* 2004; 20 (Suppl. B): 24B-28B.
56. Jongstra-Bilen J, Haidari M, Zhu S N, Chen M, Guha D, Cybulsky M I. Low-grade chronic inflammation in regions of the normal mouse arterial intima predisposed to atherosclerosis. *J Exp Med* 2006; 203: 2073-2083.
57. Santerre R F, Nicolosi R J, Smith S C. Respiratory control in preatherosclerotic susceptible and resistant pigeon aortas. *Exp Mol Pathol* 1974; 20: 397-406.
58. Droge W. Free radicals in the physiological control of cell function. *Physiol Rev* 2002; 82: 47-95.
59. Nohl H. Generation of superoxide radicals as byproducts of cellular respiration. *Ann Biol Clin* (Paris) 1994; 52: 199-204.

60. Echtay K S, Roussel D, St-Pierre J, Jekabsons M B, Cadenas S, Stuart J A, Harper J A, Roebuck S J, Morrison A, Pickering S, Clapham J C, Brand M D. Superoxide activates mitochondrial uncoupling proteins. *Nature* 2002; 415: 96-99.

61. Murphy M P, Echtay K S, Blaikie F H, Asin-Cayuela J, Cocheme H M, Green K, Buckingham J A, Taylor E R, Hurrell F, Hughes G. Miwa S, Cooper C E, Svistunenko D A, Smith R A, Brand M D. Superoxide activates uncoupling proteins by generating carbon-centered radicals and initiating lipid peroxidation: studies using a mitochondria-targeted spin trap derived from alpha-phenyl-N-tert-butylnitrone. *J Biol Chem* 2003; 278: 48534-48545.

62. Nishikawa T, Edelstein D, Du X L, Yamagishi S, Matsumura T, Kaneda Y, Yorek M A, Beebe D, Oates P J, Hammes H P, Giardino I, Brownlee M. Normalizing mitochondrial superoxide production blocks three pathways of hyperglycaemic damage. *Nature* 2000; 404: 787-790.

63. Blanc J, Alves-Guerra M C, Esposito B, Rousset S, Gourdy P, Rixquier D, Tedgui A, Miroux B, Mallat Z. Protective role of uncoupling protein 2 in atherosclerosis. *Circulation* 2003; 107: 388-390.

64. Petterson G. Effect of dinitrophenol and anoxia on isometric tension in rabbit colon smooth muscle. *Acta Pharmacol Toxicol (Copenh.)* 1985; 57: 184-189.

65. Bernal-Mizrachi C, Gates A C, Weng S, Imamura T, Knutsen R H, DeSantis P, Coleman T, Townsend R R, Muglia L J, Semenkovich C F. Vascular respiratory uncoupling increases blood pressure and atherosclerosis. *Nature* 2006; 435: 502-506.

66. Watts H. In: *Evolution of the Atherosclerotic Plaque* (ed. Jones R J) 117, 1963; Univ Chicago, Chicago.

67. Levin M, Leppanen O, Evaldsson M, Wiklund O, Bondjers G, Bjornheden T. Mapping of ATP, glucose, glycogen, and lactate concentrations within the arterial wall. *Arterioscler Thromb Vasc Biol* 2003; 25: 1801-1807.

68. Jennings R B, Kaltenbach J P, Sommens H M. Mitochondrial metabolism in ischemic injury. *Arch Pathol* 1967; 84: 15-19.

69. Smith E B. The effects of age and of early atheromata on the intimal lipids in men. *Biochem J* 1962; 84: 49p.

70. Smith E B. Lipids carried by S10-12 lipoprotein in normal and hypercholesterolaemic serum. *Lancet* 1962; 2: 530-534.

71. Klein P D, Johnson R M. Phosphorous metabolism in unsaturated fatty acid-deficient rats. *J Biol Chem* 1954; 211: 103-110.

72. Hayashida T, Portman O W. Swelling of liver mitochondria from rats fed diets deficient in essential fatty acids. *Proc Soc Exp Biol Med* 1960; 103: 656-659.

73. Cornwell D G, Panganamala R V. Atherosclerosis an intracellular deficiency in essential fatty acids. *Prog Lipid Res* 1981; 20: 365-376.

74. Das U N. Essential fatty acids—a review. *Current Pharmaceutical Biotech* 2006; 7: 467-482.

75. Felton C V, Crook D, Davies M J, Oliver M F. Relation of plaque lipid composition and morphology to the stability of human aortic plaques. *Arterioscler Thromb Vasc Biol* 1997; 17: 1337-1345.

76. Thies F, Garry J M, Yaqoob P, Rerkasem K, Williams J, Shearman C P, Gallagher P J, Calder P C, Grimble R F. Association of n-3 polyunsaturated fatty acids with stability of atherosclerotic plaques: a randomised controlled trial. *Lancet* 2003; 361: 477-485.

77. Mozaffarian D. Trans fatty acids—effects on systemic inflammation and endothelial function. *Atheroscler Suppl* 2006; 7: 29-32.

78. Mozaffarian D, Rimm E B, King I B, Lawler R L, McDonald G B, Levy W C. Trans fatty acids and systemic inflammation in heart failure. *Am J Clin Nutr* 2004; 80: 1521-1525.

79. Willett W C, Stampfer M J, Manson J E, Colditz G A, Speizer F E, Rosner B A, Sampson L A, Hennekens C H. Intake of trans fatty acids and risk of coronary heart disease among women. *Lancet* 1993; 341: 581-585.

80. Ascherio A, Hennekens C H, Buring J E, Master C, Stampfer M J, Willett W C. Trans-fatty acids intake and risk of myocardial infarction. *Circulation* 1994; 89: 94-101.

81. Das U N. Beneficial effect(s) of n-3 fatty acids in cardiovascular diseases: but, why and how? *Prostaglandins Leukot Essen Fatty Acids* 2000; 63: 351-362.

82. Juan H, Sametz W. Dihomo-gamma-linolenic acid increases the metabolism of eicosapentaenoic acid in perfused vascular tissue. *Prostaglandins Leukotrienes Med* 1985; 19: 79-86.

83. Das U N. Minerals, trace elements, and vitamins interact with essential fatty acids and prostaglandins to prevent hypertension, thrombosis, hypercholesterolemia, and atherosclerosis and their attendant complications. *Med Sci Res* 1985; 13: 684-687.

84. Bordet J C, Guichardant M, Lagarde M. Hydroperoxides produced by n-6 lipoxygenation of arachidonic and linoleic acids potentiate synthesis of prostacyclin related compounds. *Biochim Biophys Acta* 1988; 958: 460-468.

85. Bordet J C, Guichardant M, Lagarde M. Arachidonic acid strongly stimulates prostaglandin $I_3$ ($PGI_3$) production from eicosapentaenoic acid in human endothelial cells. *Biochem Biophys Res Commun* 1986; 135: 403-410.

86. Das U N. Essential fatty acids as possible mediators of the actions of statins. *Prostaglandins Leukot Essen Fatty Acids* 2001; 65: 37-40.

87. Levine L. Statins stimulate arachidonic acid release and prostaglandin I2 production in rat liver cells. *Lipids Health Dis* 2003; 2: 1.

88. Jula A, Marniemi J, Ronnemaa T, Virtanen A, Huupponen R. Effects of diet and simvastatin on fatty acid composition in hypercholesterolemic men: a randomized controlled trial. *Arterioscler Thromb Vasc Biol* 2005; 25: 1952-1959.

89. Harris J I, Hibbeln J R, Mackey R H, Muldoon M F. Statin treatment alters serum n-3 and n-6 fatty acids in hypercholesterolemic patients. *Prostaglandins Leukot Essent Fatty Acids* 2004; 71: 263-269.

90. Bellini M J, Polo M P, de Alaniz M J, de Bravo M G. Effect of simvastatin on the uptake and metabolic conversion of palmitic, dihomo-gamma-linoleic and alpha-linolenic acids in A549 cells. *Prostaglandins Leukot Essent Fatty Acids* 2003; 69: 351-367.

91. Rise P, Pazzucconi F, Sirtori C R, Galli C. Statins enhance arachidonic acid synthesis in hypercholesterolemic patients. *Nutr Metab Cardiovasc Dis* 2001; 11: 88-94.

92. Birnbaum Y, Ye Y, Lin Y, Freeberg S Y, Nishi S P, Martinez J D, Huang M H, Uretsky B F, Perez-Polo J R. Augmentation of myocardial production of 15-epi-lipoxin-$A_4$ by pioglitazone and atorvastatin in the rat. *Circulation* 2006; 114: 929-935.

93. Morris T, Stables M, Gilroy D W. New perspectives on aspirin and the endogenous control of acute inflammatory resolution. *Scientific World J* 2006; 6: 1048-1065.

94. Schwab J M, Serhan C N. Lipoxins and new lipid mediators in the resolution of inflammation. *Curr Opin Pharmacol* 2006; 6: 414-420.

95. Serhan C N. Novel omega—3-derived local mediators in anti-inflammation and resolution. *Pharmacol Ther* 2005; 105: 7-21.
96. Mozaffarian D, Pischon T, Hankinson S E, Rifai N, Joshipura K, Willett W C, Rimm E B. Dietary intake of trans fatty acids and systemic inflammation in women. *Am J Clin Nutr* 2004; 79: 606-612.
97. Baer D J, Judd J T, Clevidence B A, Tracy R P. Dietary fatty acids affect plasma markers of inflammation in healthy men fed controlled diets: a randomized crossover study. *Am J Clin Nutr* 2004; 79: 969-973.
98. Lopez-Garcia E, Schulze M B, Meigs J B, Manson J E, Rifai N, Stampfer M J, Willett W C, Hu F B. Consumption of trans fatty acids is related to plasma biomarkers of inflammation and endothelial dysfunction. *J Nutr* 2005; 135: 562-566.
99. Lopez-Garcia E, Schultze M B, Manson J E, Meigs J B, Albert C M, Rifai N, Willett W C, Hu F B. Consumption of (n-3) fatty acids is related to plasma biomarkers of inflammation and endothelial activation in women. *J Nutr* 2004; 134: 1806-1811.
100. Kumar G S, Das U N, Kumar K V, Madhavi, Das N P, Tan B K H. Effect of n-6 and n-3 fatty acids on the proliferation and secretion of TNF and IL-2 by human lymphocytes in vitro. *Nutrition Res* 1992; 12: 815-823.
101. Kumar G S, Das U N. Effect of prostaglandins and their precursors on the proliferation of human lymphocytes and their secretion of tumor necrosis factor and various interleukins. *Prostaglandins Leukot Essent Fatty Acids* 1994; 50: 331-334.
102. Harris W S. Fish oils and plasma lipid and lipoprotein metabolism in humans: a critical review. *J Lipid Res* 1989; 30: 785-807.
103. Sanders T A B, Hinds A, Pereira C C. Influence of n-3 fatty acids on blood lipids in normal subjects. *J Intern Med* 1989; 225 (suppl 1): 99-104.
104. Putadechakum S, Tanphaichitr V, Leelahagul P, Pakpeankitvatana V, Surapisitchart T, Komindr S. Long-term treatment of N-3 PUFAS on plasma lipoprotein levels and fatty acid composition of total serum and erythrocyte lipids in hypertriglyceridemic patients. *J Med Assoc Thai* 2005; 88: 181-186.
105. Roche H M, Gibney M J. Effect of long-chain n-3 polyunsaturated fatty acids on fasting and postprandial triacylglycerol metabolism. *Am J Clin Nutr* 2000; 71 (1 Suppl): 232S-237S.
106. Wilkinson P, Leach C, Ah-Sing N, Hussain N, Miller G J, Millward D J, Griffin B A. Influence of alpha-linolenic acid and fish-oil on markers of cardiovascular risk in subjects with an atherogenic lipoprotein phenotype. *Atherosclerosis* 2005; 181: 115-124.
107. Laidlaw M, Holub B J. Effects of supplementation with fish oil-derived n-3 fatty acids and gamma-linolenic acid on circulating plasma lipids and fatty acid profiles in women. *Am J Clin Nutr* 2003; 77: 37-42.
108. GISSI Prevenzione Investigators. Dietary supplementation with n-3 polyunsaturated fatty acids and vitamin E after myocardial infarction: results of the GISSI-Prevenzione trial. *Lancet* 1999; 354: 447-455.
109. Davidson M H. Mechanisms for the hypertriglyceridemic effect of marine omega-3 fatty acids. *Am J Cardiol* 2006; 98 suppl: 27i-33i.
110. Leaf A, Weber P C. Cardiovascular effects of n-3 fatty acids. *N Engl J Med* 1988; 322: 697-698.
111. Dyerberg J, Bang H O. Haemostatic function and platelet polyunsaturated fatty acids in Eskimos. *Lancet* 1979; ii: 433-435.
112. Fischer S, Weber P C, Dyerberg J. The prostacyclin/thromboxane balance is favourably shifted in Greenland Eskimos. *Prostaglandins* 1986; 32: 235-241.
113. Kristensen S D, Schmidt E B, Dyerberg J. Dietary supplementation with n-3 polyunsaturated fatty acids and human platelet function: a review with particular emphasis on implications for cardiovascular disease. *J Intern Med* 1989; 225 (suppl): 141-150.
114. Scheurlen M, Kirchner M, Clemens M R, Jaschonek K. Fish oil preparations rich in docosahexaenoic acid modify platelet responsiveness to prostaglandin-endoperoxide/thromboxane A2 receptor agonists. *Biochem Pharmacol* 1993; 46: 245-249.
115. Lefevre M, Kris-Etherton P M, Zhao G, Tracy R P. Dietary fatty acids, hemostasis, and cardiovascular disease risk. *J Am Diet Assoc* 2004; 104: 410-419.
116. Tholstrup T, Miller G J, Bysted A, Sandstrom B. Effect of individual dietary fatty acids on postprandial activation of blood coagulation factor VII and fibrinolysis in healthy young men. *Am J Clin Nutr* 2003; 77: 1125-1132.
117. Junker R, Pieke B, Schulte H, Nofer R, Neufeld M, Assmann G, Wahrburg U. Changes in hemostasis during treatment of hypertriglyceridemia with a diet rich in monounsaturated and n-3 polyunsaturated fatty acids in comparison with a low-fat diet. *Thromb Res* 2001; 101: 355-366.
118. Prichard B N C, Smith C C T, Ling K L E, Betteridge D J. Fish oils and cardiovascular disease. *BMJ* 1995; 310: 819-820.
119. Ambring A, Johansson M, Axelsen M, Gan L, Strandvik B, Friberg P. Mediterranean-inspired diet lowers the ratio of serum phospholipid n-6 to n-3 fatty acids, the number of leukocytes and platelets, and vascular endothelial growth factor in healthy subjects. *Am J Clin Nutr* 2006; 83: 575-581.
120. De Caterina R, Massaro M. Omega-3 fatty acids and the regulation of expression of endothelial pro-atherogenic and pro-inflammatory genes. *J Membr Biol* 2005; 206:103-116.
121. Chen W, Esselman W J, Jump D B, Busik J V. Anti-inflammatory effect of docosahexaenoic acid on cytokine-induced adhesion molecule expression in human retinal vascular endothelial cells. *Invest Ophthalmol Vis Sci* 2005; 46: 4342-4347.
122. Weber C, Erl W, Pietsch A, Danesch U, Weber P C. Docosahexaenoic acid selectively attenuates induction of vascular cell adhesion molecule-1 and subsequent monocytic cell adhesion to human endothelial cells stimulated by tumor necrosis factor-alpha. *Arterioscler Thromb Vasc Biol* 1995; 15: 622-628.
123. Eschen O, Christensen J H, De Caterina R, Schmidt E B. Soluble adhesion molecules in healthy subjects: a dose-response study using n-3 fatty acids. *Nutr Metab Cardiovasc Dis* 2004; 14: 180-185.
124. Johansen O, Seljeflot I, Hostmark A T, Arnesen H. The effect of supplementation with omega-3 fatty acids on soluble markers of endothelial function in patients with coronary heart disease. *Arterioscler Thromb Vasc Biol* 1999; 19: 1681-1686.
125. Morisaki N, Sprecher H, Milo G E, Cornwell D G. Fatty acid specificity in the inhibition of cell proliferation and its relationship to lipid peroxidation and prostaglandin biosynthesis. *Lipids* 1982; 17: 893-899.
126. Cornwell D G, Panganamala R V. Atherosclerosis: an intracellular deficiency in essential fatty acids. *Prog Lipid Res* 1981; 20: 365-376.

127. Hirafuji M, Machida T, Hamaue N, Minami M. Cardiovascular protective effects of n-3 polyunsaturated fatty acids with special emphasis on docosahexaenoic acid. *J Pharmacol Sci* 2003; 92: 308-316.

128. Abeyawardena M Y, Head R J. Long chain n-3 polyunsaturated fatty acids and blood vessel function. *Cardiovasc Res* 2001; 52: 361-371.

129. Pakala R, Pakala R, Sheng W L, Benedict C R. Eicosapentaenoic acid and docosahexaenoic acid block serotonin-induced smooth muscle cell proliferation. *Arterioscler Thromb Vasc Biol* 1999; 19: 2316-2322.

130. Nakayama M, Fukuda N, Watanabe Y, Soma M, Hu W Y, Kishioka H, Satoh C, Kubo A, Kamatsuse K. Low dose of eicosapentaenoic acid inhibits exaggerated growth of Vascular smooth muscle cells from spontaneously hypertensive rats through suppression of transforming growth factor-beta. *J Hypertens* 1999; 17: 1421-1430.

131. Nobukata H, Ishikawa T, Obata M, Shibutani Y. Long-term administration of highly purified eicosapentaenoic acid ethyl ester improves the dysfunction of vascular endothelial and smooth muscle cells in male WBN/Kob rats. *Metabolism* 2000; 49: 1588-1591.

132. Mori Y, Nobukata H, Harada T, Kasahara T, Tajima N. Long-term administration of highly purified eicosapentaenoic acid ethyl ester improves blood coagulation abnormalities and dysfunction of vascular endothelial cells in Otsuka Long-Evans Tokushima fatty rats. *Endocr J* 2003; 50: 603-611.

133. Huttner J J, Gwebu E T, Panganamala R V, Milo G E, Cornwell D C, Sharma H M, Geer J C. Fatty acids and their prostaglandin derivatives: inhibitors of proliferation in aortic smooth muscle cells. *Science* 1977; 197: 289-291.

134. Fan Y Y, Ramos K S, Chapkin R S. Dietary gamma-linolenic acid suppresses aortic smooth muscle cell proliferation and modifies atherosclerotic lesions in apolipoprotein E knockout mice. *J Nutr* 2001; 131: 1675-16781.

135. Das U N. Is angiotensin H an endogenous pro-inflammatory molecule? *Med Sci Monit* 2005; 11: RA155-RA162.

136. Kumar K V, Das U N. Effect of cis-unsaturated fatty acids, prostaglandins, and free radicals on angiotensin-converting enzyme activity in vitro. *Proc Soc Exp Biol Med* 1997; 214: 374-379.

137. Okuda Y, Kawashima K, Sawada T, Tsurumaru K, Asano M, Suzuki S, Soma M, Nakajima T, Yamashita K. Eicosapentaenoic acid enhances nitric oxide production by cultured human endothelial cells. *Biochem Biophys Res Commun* 1997; 232: 487-491.

138. Das, U. N. *A Perinatal Strategy for Preventing Adult Diseases: The Role of Long-Chain Polyunsaturated Fatty Acids*. Kluwer Academic Publishers, Boston, 2002.

139. Das U N, Mohan I K, Raju T R. Effect of corticosteroids and eicosapentaenoic acid/docosahexaenoic acid on pro-oxidant and anti-oxidant status and metabolism of essential fatty acids in patients with glomerular disorders. *Prostaglandins Leukot Essen Fatty Acids* 2001:65:197-203.

140. Bunk, S. ACEs wild. *The Scientist* 2002; 16: 22-24.

141. Moskowitz, D. W. Is angiotensin I-converting enzyme a 'master' disease gene? *Diabetes Tech Therapeutics* 2002; 4: 683-711.

142. Kaergel E, Muller D N, Honeck H, Theuer J, Shagdarsuren E, Mullally A, Luft F C, Schunck W-H. P450-dependent arachidonic acid metabolism and angiotensin-H-induced renal damage. *Hypertension* 2002; 40: 273-279.

143. Gilroy D W: New insights into the anti-inflammatory actions of aspirin-induction of nitric oxide through the generation of epi-lipoxins. *Mem Inst Oswaldo Cruz* 2005; 100 Suppl 1: 49-54.

144. Wang W, Diamond S L. Does elevated nitric oxide production enhance the release of prostacyclin from shear stressed aortic endothelial cells? *Biochem Biophys Res Commun* 1997; 233: 748-751.

145. Arita M, Bianchini F, Aliberti J, Sher A, Chiang N, Hong S, Yang R, Petasis N A, Serhan C N. Stereochemical assignment, antiinflammatory properties, and receptor for the omega-3 lipid mediator resolvin E1. *J Exp Med* 2005; 201: 713-722.

146. Dooper, M. M; van Riel, B; Graus, Y. M; M'Rabet, L. Dihomo-gamma-linolenic acid inhibits tumour necrosis factor-alpha production by human leucocytes independently of cyclooxygenase activity. *Immunology* 2003; 110: 348-357.

147. Chen W, Esselman W J, Jump D B, Busik J V. Anti-inflammatory effect of docosahexaenoic acid on cytokine-induced adhesion molecule expression in human retinal vascular endothelial cells. *Invest Ophthalmol V is Sci* 2005; 46: 4342-4347.

148. Li H, Ruan X Z, Powis S H, Fernando R, Mon W Y, Wheeler D C, Moohead J F, Varghese Z. EPA and DHA reduce LPS-induced inflammation responses in HK-2 cells: evidence for a PPAR-gamma-dependent mechanism. *Kidney Int* 2005; 67: 867-874.

149. Sheng Z, Otani H, Brown M S, Goldstein J L. Independent regulation of sterol regulatory element-binding proteins 1 and 2 in hamster liver. *Proc Natl Acad Sci USA* 1995; 92: 935-938.

150. Fajas L, Schoonjans K, Gelman L, Kim J B, Najib J, Martin G, Fruchart J C, Briggs M, Spiegelman B M, Auwerx J. Regulation of peroxisome proliferator-activated receptor gamma expression by adipocyte differentiation and determination factor 1/sterol regulatory element binding protein 1: implications for adipocyte differentiation and metabolism. *Mol Cell Biol* 1999; 19: 5495-5503.

151. El-Sohemy A, Archer M C. Regulation of mevalonate synthesis in low density lipoprotein receptor knockout mice fed n-3 or n-6 polyunsaturated fatty acids. *Lipids* 1999; 34: 1037-1043.

152. Nakamura N, Hamazaki T, Jokaji H, Minami S, Kobayashi M. Effect of HMG-CoA reductase inhibitors on plasma polyunsaturated fatty acid concentration in patients with hyperlipidemia. *Int J Clin Lab Res* 1998; 28: 192-195.

153. Das U N. Essential fatty acids and osteoporosis. *Nutrition* 2000; 16: 286-290.

154. Hannah V C, Ou J, Luong A, Goldstein J L, Brown M S. Unsaturated fatty acids down-regulate srebp isoforms 1a and 1c by two mechanisms in HEK-293 cells. *J Biol Chem* 2001; 276: 4365-4372.

155. Field F J, Born E, Murthy S, Mathur S N. Polyunsaturated fatty acids decrease the expression of sterol regulatory element-binding protein-1 in CaCo-2 cells: effect on fatty acid synthesis and triacylglycerol transport. *Biochem J* 2002; 368 (Pt 3): 855-864.

156. Xu J, Cho H, O'Malley S, Park J H, Clarke S D. Dietary polyunsaturated fats regulate rat liver sterol regulatory element binding proteins-1 and -2 in three distinct stages and by different mechanisms. *J Nutr* 2002; 132: 3333-3339.

157. Field F J, Born E, Mathur S N. Fatty acid flux suppresses fatty acid synthesis in hamster intestine independently of SREBP-1 expression. *J Lipid Res* 2003; 44: 1199-1208.

158. Le Jossic-Corcos C, Gonthier C, Zaghini I, Logette E, Shechter I, Bournot P. Hepatic farnesyl diphosphate synthase expression is suppressed by polyunsaturated fatty acids. *Biochem J* 2005; 385 (Pt 3): 787-794.
159. Worgall T S, Johnson R A, Seo T, Gierens H, Deckelbaum R J. Unsaturated fatty acid-mediated decreases in sterol regulatory element-mediated gene transcription are linked to cellular sphingolipid metabolism. *J Biol Chem* 2002; 277: 3878-3885.
160. Matsuzaka T, et al. Dual expression of mouse $\Delta^5$ and $\Delta^6$-desaturase gene expression by SREBP-1 and PPARα. *J Lipid Res* 2002; 43: 107-114.
161. Leonard A E, Kelder B, Bobik E G, Chuang L T, Parker-Barnes J M, Thurmond J M, Kroeger P E, Kopchick J J, Huang Y S, Mukerji P. cDNA cloning and characterization of human $\Delta^5$-desaturase involved in the biosynthesis of arachidonic acid. *Biochem J* 2000; 347: 719-724.
162. Cho H P, Nakamura M, Clarke S D. Cloning, expression, and fatty acid regulation of the human $\Delta^5$-desaturase. *J Biol Chem* 1999; 274: 37335-37339.
163. Cho H P, Nakamura M T, Clarke S D. Cloning, expression, and nutritional regulation of the mammalian $\Delta^6$-desaturase. *J Biol Chem* 1999; 274: 471-477.
164. Sayanova O, Beaudoin F, Libisch B, Castel A, Shewry P R, Napier P A. Mutagenesis and heterologous expression in yeast of a plant $\Delta^6$-fatty acid desaturase. *J Exp Botany* 2001; 52: 1581-1585.
165. Sayanova O, Smith M A, Lapinskas P, Stobart A K, Dobson G, Christie W W, Shewry P R, Napier J A. Expression of a borage desaturase cDNA containing an N-terminal cytochrome b5 results in the accumulation of high levels of delta-6-desaturated fatty acids in transgenic tobacco. *Proc Natl Acad Sci USA* 1997; 94: 4211-4216.
166. Sayanova O, Shewry P R, Napier J A. Histidine-41 of the cytochrome b5 domain of the borage $\Delta^6$ fatty acid desaturase is essential for enzyme activity. *Plant Physiol* 1999; 121: 641-646.
167. Beaudoin F, Michaelson L V, Hey S J, Lewis M J, Shewry P R, Sayanova O, Napier J A. Heterologous reconstitution in yeast of the polyunsaturated fatty acid Biosynthetic pathway. *Proc Natl Acad Sci USA* 2000; 97: 6421-6426.
168. Tang C, Cho H P, Nakamura M T, Clarke S D. Regulation of human Δ-6 desaturase gene transcription: identification of a functional direct repeat-1 element. *J Lipid Res* 2003; 44: 686-695.
169. Schaeffer L, Gohlke H, Muller M, Heid I M, Palmer L J, Kompauer I, Demmelmair H, Illig T, Koletzko B, Heinrich J. Common genetic variants of the FADS1 FADS2 gene cluster and their reconstructed haplotypes are associated with the fatty acid composition in phospholipids. *Hum Mol Genet.* 2006; 15: 1745-1756.

TABLE 1

Summary of effects of PUFAs on nuclear receptors involved in the regulation of lipogenesis.

| Nuclear receptor | Effects on gene regulation | Expected changes | | |
|---|---|---|---|---|
| | | TG | HDL | LDL |
| PPAR-α | ↑ | ↓↓ | ↑ | ↓ |
| LXR | ↓ | ↓↓ | ↓ | ↓ |
| FXR | ↑ | ↓↓ | ↑ | ↑ |
| HNF-4α | ↓ | ↓↓ | ↓ | ↔ |
| Net effects | | ↓↓↓↓ | ↔ | ↔ |

FXR = Farnesol X receptor;
HDL = High-density lipoprotein;
HNF-4α = Hepatocyte nuclear factor-4α;
LDL = Low-density lipoprotein;
LXR = Liver X receptor;
PPAR-α = Peroxisome proliferator-activated receptor;
↑ = Increase;
↓ = Decrease;
↔ = Neutral effect.

The invention claimed is:

1. A method of detecting, diagnosing and prognosticating atherosclerosis by measuring the activities of the enzymes $\Delta^6$ and $\Delta^5$ desaturases in tissue(s) such as platelets, leukocytes, blood vessels including endothelial cells, wherein decreased activities of $\Delta^6$ and $\Delta^5$ desaturases in a subject as compared to normal ones is a means of detection, diagnosis or prognosis of atherosclerosis.

2. The method of claim 1, wherein the activity of the enzymes $\Delta^6$ and $\Delta^5$ desaturases is measured by estimating the ratio between fatty acids γ-linolenic acid (GLA) and linoleic acid (LA) of ω-6 series and/or, stearidonic acid (SA, 18:4) and α-linolenic acid (ALA) of ω-3 series for $\Delta^6$ desaturase activity (LA/GLA and/or SA/ALA=$\Delta^6$ desaturase activity); and the ratio between dihomo-γ-linolenic acid (DGLA) and arachidonic acid (AA) of ω-6 series and 20:4 ω-3 and EPA for $\Delta^5$ desaturase activity (DGLA/AA and/or 20:4 ω-3/EPA=$\Delta^5$ desaturase activity).

3. The method of claim 2, wherein the fatty acids linoleic acid, γ-linolenic acid, dihomo-γ-linolenic acid and arachidonic acid of ω-6 series and α-linolenic acid, stearidonic acid, 20:4 ω-3, eicosapentaenoic acid and docosahexaenoic acid of ω-3 series are measured in the plasma, and cell membranes of leukocytes, platelets, endothelial cells and red blood cells.

4. The method as in claim 1, wherein the activities of the enzymes $\Delta^6$ and $\Delta^5$ desaturases is assessed by measuring the metabolites of polyunsaturated fatty acids prostaglandin $E_1$, prostacyclin ($PGI_2$), prostaglandin $I_3$, lipoxins, resolvins, protectins and nitrolipids in the plasma, leukocytes, platelets and endothelial cells.

* * * * *